US010342502B2

(12) United States Patent
Dascal et al.

(10) Patent No.: US 10,342,502 B2
(45) Date of Patent: Jul. 9, 2019

(54) X-RAY IMAGE FEATURE DETECTION AND REGISTRATION SYSTEMS AND METHODS

(71) Applicant: LightLab Imaging, Inc., Westford, MA (US)

(72) Inventors: Lorina Dascal, Haifa (IL); Itai Winkler, Haifa (IL)

(73) Assignee: Lightlab Imaging, Inc., Westford, MA (US)

(*) Notice: Subject to any disclaimer, the term of this patent is extended or adjusted under 35 U.S.C. 154(b) by 0 days.

(21) Appl. No.: 15/355,970

(22) Filed: Nov. 18, 2016

(65) Prior Publication Data

US 2017/0140531 A1    May 18, 2017

Related U.S. Application Data

(60) Provisional application No. 62/257,213, filed on Nov. 18, 2015.

(51) Int. Cl.
*G06K 9/00* (2006.01)
*A61B 6/00* (2006.01)
(Continued)

(52) U.S. Cl.
CPC ........ *A61B 6/5247* (2013.01); *A61B 5/0066* (2013.01); *A61B 6/504* (2013.01);
(Continued)

(58) Field of Classification Search
CPC ................... G06T 2207/10116; A61B 6/5247
See application file for complete search history.

(56) References Cited

U.S. PATENT DOCUMENTS

| 5,321,501 A | 6/1994 | Swanson et al. |
| 5,459,570 A | 10/1995 | Swanson et al. |

(Continued)

FOREIGN PATENT DOCUMENTS

| WO | 2012176191 | 12/2012 |
| WO | 2013175472 | 11/2013 |
| WO | 2014002095 | 3/2014 |

OTHER PUBLICATIONS

Shengxian Tu et al., "In vivo comparison of arterial lumen dimensions assessed by co-registered three-dimensional (3D) quantitative coronary angiography, intravascular ultrasound and optical coherence tomography", Int. J. Cardiovasc Imaging (2012) 28:1315-1327.

(Continued)

*Primary Examiner* — Oneal R Mistry
(74) *Attorney, Agent, or Firm* — K&L Gates LLP

(57) ABSTRACT

The disclosure relates generally to the field of vascular system and peripheral vascular system data collection, imaging, image processing and feature detection relating thereto. In part, the disclosure more specifically relates to methods for detecting position and size of contrast cloud in an x-ray image including with respect to a sequence of x-ray images during intravascular imaging. Methods of detecting and extracting metallic wires from x-ray images are also described herein such as guidewires used in coronary procedures. Further, methods for of registering vascular trees for one or more images, such as in sequences of x-ray images, are disclosed. In part, the disclosure relates to processing, tracking and registering angiography images and elements in such images. The registration can be performed relative to images from an intravascular imaging modality such as, for example, optical coherence tomography (OCT) or intravascular ultrasound (IVUS).

18 Claims, 21 Drawing Sheets

(51) Int. Cl.
*G06T 7/00* (2017.01)
*A61B 5/00* (2006.01)
*A61B 8/12* (2006.01)
*G06T 5/50* (2006.01)

(52) U.S. Cl.
CPC .............. *A61B 8/12* (2013.01); *G06T 5/50* (2013.01); *G06T 7/0012* (2013.01); *G06T 2207/10101* (2013.01); *G06T 2207/10116* (2013.01); *G06T 2207/30101* (2013.01)

(56) References Cited

U.S. PATENT DOCUMENTS

| | | |
|---|---|---|
| 5,465,147 A | 11/1995 | Swanson |
| 5,509,093 A | 4/1996 | Miller et al. |
| 5,586,201 A | 12/1996 | Whiting et al. |
| 5,619,368 A | 4/1997 | Swanson |
| 5,715,827 A | 2/1998 | Corl et al. |
| 5,748,598 A | 5/1998 | Swanson et al. |
| 5,784,352 A | 7/1998 | Swanson et al. |
| 5,822,391 A | 10/1998 | Whitting |
| 5,956,355 A | 9/1999 | Swanson et al. |
| 6,111,645 A | 8/2000 | Tearney et al. |
| 6,134,003 A | 10/2000 | Tearney et al. |
| 6,148,095 A | 11/2000 | Prause et al. |
| 6,160,826 A | 12/2000 | Swanson et al. |
| 6,191,862 B1 | 2/2001 | Swanson et al. |
| 6,195,445 B1 | 2/2001 | Jolly et al. |
| 6,282,011 B1 | 8/2001 | Tearney et al. |
| 6,302,875 B1 | 10/2001 | Makower et al. |
| 6,421,164 B2 | 7/2002 | Tearney et al. |
| 6,445,939 B1 | 9/2002 | Swanson et al. |
| 6,485,413 B1 | 11/2002 | Boppart et al. |
| 6,501,551 B1 | 12/2002 | Tearney et al. |
| 6,552,796 B2 | 4/2003 | Magnin et al. |
| 6,564,087 B1 | 5/2003 | Pitris et al. |
| 6,565,514 B2 | 5/2003 | Svanerudh et al. |
| 6,570,659 B2 | 5/2003 | Schmitt |
| 6,706,004 B2 | 3/2004 | Tearney et al. |
| 6,728,566 B1 | 4/2004 | Subramanyan et al. |
| 6,731,973 B2 | 5/2004 | Voith |
| 6,879,851 B2 | 4/2005 | McNamara et al. |
| 6,891,984 B2 | 5/2005 | Petersen et al. |
| 6,937,696 B1 | 8/2005 | Mostafavi |
| 6,973,202 B2 | 12/2005 | Mostafavi |
| 7,068,831 B2 | 6/2006 | Florent et al. |
| 7,134,994 B2 | 11/2006 | Alpert et al. |
| 7,191,100 B2 | 3/2007 | Mostafavi |
| 7,208,333 B2 | 4/2007 | Flanders et al. |
| 7,231,243 B2 | 6/2007 | Tearney et al. |
| 7,241,286 B2 | 7/2007 | Atlas |
| 7,301,644 B2 | 11/2007 | Knighton et al. |
| 7,321,677 B2 | 1/2008 | Evron et al. |
| 7,414,779 B2 | 8/2008 | Huber et al. |
| 7,415,049 B2 | 8/2008 | Flanders et al. |
| RE40,608 E | 12/2008 | Glover et al. |
| 7,593,559 B2 | 9/2009 | Toth et al. |
| 7,625,366 B2 | 12/2009 | Atlas |
| 7,697,972 B2 | 4/2010 | Verard et al. |
| 7,729,746 B2 | 6/2010 | Redel et al. |
| 7,742,797 B2 | 6/2010 | Redel et al. |
| 7,792,342 B2 | 9/2010 | Barbu et al. |
| 7,813,609 B2 | 10/2010 | Petersen et al. |
| 7,848,791 B2 | 12/2010 | Schmitt et al. |
| 7,869,663 B2 | 1/2011 | Buckland et al. |
| 7,872,759 B2 | 1/2011 | Tearney et al. |
| 7,916,387 B2 | 3/2011 | Schmitt et al. |
| 7,918,793 B2 | 4/2011 | Altmann et al. |
| 7,925,327 B2 | 4/2011 | Weese |
| 7,930,014 B2 | 4/2011 | Huennekens et al. |
| 7,935,060 B2 | 5/2011 | Schmitt et al. |
| 7,988,633 B2 | 8/2011 | Hossack et al. |
| 7,991,105 B2 | 8/2011 | Mielekamp et al. |
| 8,029,447 B2 | 10/2011 | Kanz et al. |
| 8,116,605 B2 | 2/2012 | Petersen et al. |
| 8,206,374 B2 | 6/2012 | Duane et al. |
| 8,206,377 B2 | 6/2012 | Petroff |
| 8,259,303 B2 | 9/2012 | Johnson et al. |
| 8,290,228 B2 | 10/2012 | Cohen et al. |
| 8,298,147 B2 | 10/2012 | Huennekens et al. |
| 8,325,419 B2 | 12/2012 | Schmitt |
| 8,351,665 B2 | 1/2013 | Tearney et al. |
| 8,358,461 B2 | 1/2013 | Huber et al. |
| 8,412,312 B2 | 4/2013 | Judell et al. |
| 8,423,121 B2 | 4/2013 | Wang et al. |
| 8,449,468 B2 | 5/2013 | Petersen et al. |
| 8,457,375 B2 | 6/2013 | Rieber et al. |
| 8,457,440 B1 | 6/2013 | Johnson |
| 8,463,007 B2 | 6/2013 | Steinberg et al. |
| 8,478,387 B2 | 7/2013 | Xu |
| 8,503,844 B2 | 8/2013 | Petersen et al. |
| 8,542,900 B2 | 9/2013 | Tolkowsky et al. |
| 8,556,820 B2 | 10/2013 | Alpert et al. |
| 8,562,537 B2 | 10/2013 | Alpert et al. |
| 8,571,639 B2 | 10/2013 | Mostafavi |
| 8,581,643 B1 | 11/2013 | Schmitt |
| 8,582,109 B1 | 11/2013 | Schmitt |
| 8,582,619 B2 | 11/2013 | Adler |
| 8,582,934 B2 | 11/2013 | Adler et al. |
| 8,670,603 B2 | 3/2014 | Tolkowsky et al. |
| 8,693,756 B2 | 4/2014 | Tolkowsky et al. |
| 8,700,130 B2 | 4/2014 | Iddan et al. |
| 8,781,193 B2 | 7/2014 | Steinberg et al. |
| 8,855,744 B2 | 10/2014 | Tolkowsky et al. |
| 8,909,323 B2 | 12/2014 | Baumgart |
| 8,913,084 B2 | 12/2014 | Chen et al. |
| 2002/0161351 A1 | 10/2002 | Samson et al. |
| 2004/0006277 A1 | 1/2004 | Langenhove et al. |
| 2005/0043614 A1 | 2/2005 | Huizenga et al. |
| 2005/0201662 A1 | 9/2005 | Petersen et al. |
| 2006/0095065 A1 | 5/2006 | Tanimura et al. |
| 2007/0024617 A1 | 2/2007 | Poole |
| 2007/0066890 A1 | 3/2007 | Maschke |
| 2007/0135803 A1 | 6/2007 | Belson |
| 2008/0221439 A1 | 9/2008 | Iddan et al. |
| 2008/0221440 A1 | 9/2008 | Iddan et al. |
| 2008/0221442 A1 | 9/2008 | Tolkowsky et al. |
| 2009/0080728 A1* | 3/2009 | Socher .............. G06K 9/6256 382/128 |
| 2009/0174931 A1 | 7/2009 | Huber et al. |
| 2009/0306520 A1 | 12/2009 | Schmitt et al. |
| 2010/0076320 A1 | 3/2010 | Petersen et al. |
| 2010/0157041 A1 | 6/2010 | Klaiman et al. |
| 2010/0160764 A1 | 6/2010 | Steinberg et al. |
| 2010/0160773 A1 | 6/2010 | Cohen et al. |
| 2010/0161022 A1 | 6/2010 | Tolkowsky et al. |
| 2010/0161023 A1 | 6/2010 | Cohen et al. |
| 2010/0172556 A1 | 7/2010 | Cohen et al. |
| 2010/0191102 A1 | 7/2010 | Steinberg et al. |
| 2010/0222671 A1 | 9/2010 | Cohen et al. |
| 2010/0228076 A1 | 9/2010 | Blank et al. |
| 2010/0290693 A1 | 11/2010 | Cohen et al. |
| 2011/0071404 A1 | 3/2011 | Schmitt et al. |
| 2011/0101207 A1 | 5/2011 | Schmitt |
| 2011/0157686 A1 | 6/2011 | Huber et al. |
| 2011/0190586 A1 | 8/2011 | Kemp |
| 2011/0228280 A1 | 9/2011 | Schmitt et al. |
| 2011/0228992 A1* | 9/2011 | Wels .................. G06T 7/12 382/128 |
| 2011/0319752 A1 | 12/2011 | Steinberg et al. |
| 2012/0004529 A1 | 1/2012 | Tolkowsky et al. |
| 2012/0004537 A1 | 1/2012 | Tolkowsky et al. |
| 2012/0029339 A1 | 2/2012 | Cohen et al. |
| 2012/0310081 A1 | 6/2012 | Adler et al. |
| 2012/0238869 A1 | 9/2012 | Schmitt et al. |
| 2012/0250028 A1 | 10/2012 | Schmitt et al. |
| 2012/0300215 A1 | 11/2012 | Johnson et al. |
| 2012/0300216 A1 | 11/2012 | Johnson et al. |
| 2013/0010303 A1 | 1/2013 | Petersen et al. |
| 2013/0012811 A1 | 1/2013 | Schmitt et al. |
| 2013/0023761 A1 | 1/2013 | Petroff |
| 2013/0051728 A1 | 2/2013 | Petroff |
| 2013/0072805 A1 | 3/2013 | Schmitt et al. |
| 2013/0123616 A1 | 5/2013 | Merritt et al. |

(56) References Cited

U.S. PATENT DOCUMENTS

| | | |
|---|---|---|
| 2013/0310698 A1 | 11/2013 | Judell et al. |
| 2014/0094660 A1 | 4/2014 | Tolkowsky et al. |
| 2014/0094689 A1 | 4/2014 | Cohen et al. |
| 2014/0094691 A1 | 4/2014 | Steinberg et al. |
| 2014/0094692 A1 | 4/2014 | Tolkowsky et al. |
| 2014/0094693 A1 | 4/2014 | Cohen et al. |
| 2014/0100451 A1 | 4/2014 | Tolkowsky et al. |
| 2014/0107479 A1 | 4/2014 | Klaiman et al. |
| 2014/0114184 A1 | 4/2014 | Klaiman et al. |
| 2014/0114185 A1 | 4/2014 | Tolkowsky et al. |
| 2014/0270436 A1* | 9/2014 | Dascal .............. G06T 7/11 382/130 |
| 2015/0179148 A1* | 6/2015 | Auvray .............. A61B 6/12 345/629 |
| 2016/0196666 A1* | 7/2016 | Venkatraghavan ...... A61B 6/12 382/130 |
| 2017/0140532 A1* | 5/2017 | Dascal .............. A61B 6/5247 |

OTHER PUBLICATIONS

International Search Report and Written Opinion mailed from the International Searching Authority dated Jun. 27, 2014 for International Application No. PCT/US2013/030623 (17 pages).

Dave Fornell, "The Advantages and Disadvantages of OCT vs. IVUS", Diagnostic and Interventional Cardiology, May 18, 2011, pp. 1-4.

Palti-Wasserman et al., "Identifying and Tracking a Guide Wire in the Coronary Arteries During Angioplasty from X-Ray Images", IEEE transactions on biomedical engineering, 44:2, Feb. 1997, pp. 152-164.

Perez-Rovira et al., "Deformable Registration of Retinal Fluorescein Angiogram Sequences Using Vasculature Structures", 32nd Annual Conf. of IEEE EMBS, 2010, pp. 4383-4386.

* cited by examiner

| OCT Frame | 0 | 1 | 2 |
|---|---|---|---|
| OCT Frame Time | 5800 | 5805 | 5811 |
| Angio-0 Index | 87 | 87 | 87 |
| Angio-0 Time | 5800 | 5800 | 5800 |
| Angio-0 Marker X | 704.16 | 703.2 | 702.23 |
| Angio-0 Marker Y | 490.43 | 488.76 | 487.1 |
| Angio-0 Score | 0.96 | 0.96 | 0.96 |
| Angio-1 Index | 88 | 88 | 88 |
| Angio-1 Time | 5867 | 5867 | 5867 |
| Angio-1 Marker X | 701.75 | 700.7 | 699.64 |
| Angio-1 Marker Y | 483.07 | 481.37 | 479.69 |
| Angio-1 Score | 0.95 | 0.95 | 0.95 |
| Angio-2 Index | 89 | 89 | 89 |
| Angio-2 Time | 5933 | 5933 | 5933 |
| Angio-2 Marker X | 685.79 | 684.79 | 683.78 |
| Angio-2 Marker Y | 477.29 | 475.56 | 473.85 |
| Angio-2 Score | 0.96 | 0.96 | 0.96 |

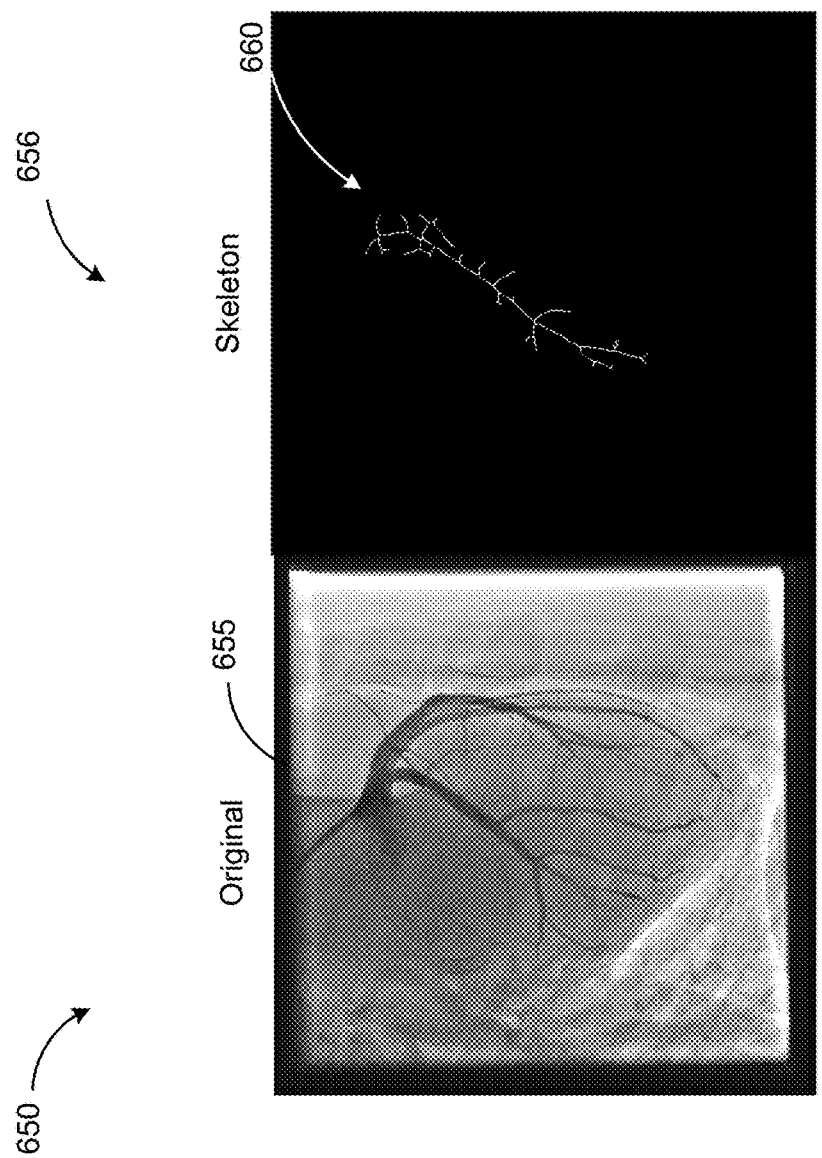

X-RAY IMAGE FEATURE DETECTION AND REGISTRATION SYSTEMS AND METHODS

CROSS-REFERENCE TO RELATED APPLICATIONS

This application claims priority to and the benefit of U.S. provisional patent application No. 62/257,213, filed on Nov. 18, 2015, the disclosure of which is herein incorporated by reference in its entirety.

FIELD

In part, the disclosure relates generally to the field of vascular system and peripheral vascular system imaging and data collection. More particularly, the disclosure relates, in part, to detection and analysis of image features.

BACKGROUND

X-ray images provide an important diagnostic tool in various disciplines. For example, interventional cardiologists use x-ray based imaging systems in various procedures and exams. As a specific type of x-ray imaging, fluoroscopy is generally used to perform angiographic imaging of blood vessels. Visualizing an artery during catheterization is a valuable diagnostic tool. Such visualization helps plan and perform catheter placement and stent deployment. As a result, achieving accurate visualization is an important technical requirement for x-ray imaging and tracking features and objects relative thereto. Numerous imaging and co-registration challenges can arise which make it difficult to achieve such accuracy. In particular, when an x-ray based imaging method is coupled with an intravascular imaging with an optical coherence tomography or ultrasound probe, the imaging and co-registration challenges become even more complex. Various factors associated with different imaging methods and devices used to position and guide imaging devices can also negatively impact registration and co-registration methods. These factors can create additional problems to address.

For example, the injection of contrast solution to enhance imaging of blood vessels via angiography can obscure optical, acoustic and other imaging probes disposed in the artery. The use of guidewires and catheters in the vasculature can also obscure certain landmarks and otherwise interfere with imaging and analysis tools. As a result, all of these factors and others make performing diagnostic intravascular imaging and registration as part of the image display and diagnostic process challenging. In addition, the challenges relating to imaging, image analysis and registration, also negatively impact stent planning and other procedures that rely on such imaging data and associated diagnostic information.

The present disclosure addresses these challenges and others.

SUMMARY

The disclosure relates generally to the field of vascular system and peripheral vascular system data collection, imaging, image processing and feature detection relating thereto. In part, the disclosure more specifically relates to methods for detecting position and size of contrast cloud in an x-ray image including with respect to a sequence of x-ray images during intravascular imaging. These techniques are useful when contrast solution is introduced into a blood vessel or other body lumen as part of various angiography or other x-ray related imaging methods. An injection or other delivery contrast solution renders the artery radiopaque for angiography or other x-ray related imaging methods. For example, in the imaging of an artery for a cardiac procedure contrast solution is introduced into one or more arteries. In part, the disclosure relates to methods for detecting contrast cloud related parameters in an x-ray image including with respect to a sequence of x-ray images. These parameters can include the position and the size of a given contrast cloud.

Methods of detecting and extracting metallic wires from x-ray images are also described herein such as guidewires used in coronary procedures. Further, methods of registering vascular trees for one or more images, such as in sequences of x-ray images, are also disclosed. In part, the disclosure relates to processing, tracking and registering angiography images and elements in such images. The registration can be performed relative to images from an intravascular imaging modality such as, for example, optical coherence tomography (OCT) or intravascular ultrasound (IVUS).

In part, the disclosure relates to detecting a contrast cloud on x-ray image frames such that the cloud containing regions of the x-ray image can be excluded from one or more subsequent x-ray image processing steps to increase cross-frame registration accuracy. The detection/identification of contract cloud regions provides for stable vessel centerlines that increase the accuracy of cross frame registration between x-ray frames. In addition, radiopaque marker detection on an x-ray image can be enhanced from more stable vessel centerlines because of contrast cloud detection. In one embodiment, vessel centerlines are also referred to as traces and vice versa.

In part, the disclosure relates to a method to register vascular trees or one or more segments of vascular trees, across multiple frames. In part, the disclosure relates to a method to extract bifurcation positions from skeletons generated from angiograms and fusion of the same bifurcation position on a series of frames. In one embodiment, the method includes eliminating false bifurcations. If not eliminated, such false bifurcation detections would otherwise be used to generate a path through the vascular tree and interfere with accurate image registration and other subsequent processing steps. In part, the disclosure relates to a method to represent bifurcation based on its characteristics (features) such as take-off angle, arc-length position, absolute angle, intensity, size (scale). In one embodiment, the take-off angle is measured relative to the parent vessel. Various image-processing methods to perform such feature extraction can be used as described herein.

In part, the disclosure relates to a method to associate the same anatomical bifurcation extracted from multiple angiograms, based on clustering in feature space, including a method for filtering excess data and completing missing representatives. In part, the disclosure relates to a method to select a suitable bifurcation cluster that can serve as one or more anchor points for improved to reduce cross-frame image registration. Cross-frame image registration facilitates continuity of position between x-ray images and allows for increased accuracy when tracking position and a reference frame for stent deployment and other intravascular procedures performed using angiography.

In one embodiment, the method further includes dilating one or more candidate regions or the fused contrast cloud region to provide a safe zone for excluding tracking of the marker. In one embodiment, the method further includes co-registering OCT image data and a plurality of the angiography image frames. In one embodiment, the method further includes the step of applying a smoothing filter to one or more angiography frames such that elements with a particular desired scale are preserved.

In one embodiment, the method further includes adaptively thresholding the smoothed image such that small-scale image elements removed to generate a binary image, wherein pixels in contrast cloud regions are of a first value or threshold such as an intensity value or threshold in the binary image. In one embodiment, the method further includes selecting a contrast cloud neighborhood and overlaying the neighborhood on one or more angiography frames to include the cloud regions having the first value in the binary image. In one embodiment, the method further includes counting or scoring an amount of pixels comprising the first value in the neighborhood. In one embodiment, the method further includes adaptively thresholding pixels comprising first value and removing pixels from each neighborhood comprising a value other than the first value.

In one embodiment, the method further includes detecting a guidewire in a plurality of angiography frames, generating one or more image masks and using such guidewire position and the one or more masks to find an anatomical stable anchor point. In one embodiment, the determined anchor point is selected as the distal end-point of the vessel centerlines. Determining such an end improves vessel centerline generation in one embodiment.

In one embodiment, the method further includes plotting a plurality of clusters associated with bifurcations and using the clusters to perform cross-frame registration between angiography frames based on arc-length interpolation between vessel segments defined between two anchor points such as bifurcations, bends and vessel centerline end-points in each frame. In one embodiment, the method further includes grouping a plurality of anatomically associated bend points, by using any suitable shortest or optical path determining algorithm, such as, for example, the Viterbi algorithm. Such an algorithm or other method can be used to determine the probable sequence of positions and the associated most probable path through the vascular section. In one embodiment, the cost criterion is based on bend angle change or curvature or a curvature analog, bend position along the vessel centerline, bend angle deviations difference between consecutive frames.

In one embodiment, the method further includes applying an image processing transform, such as a kernel matrix or other image transforming operator or matrix to one or more frames to remove or modify a feature in at least one frame. The method can include generating a mask to perform feature extraction during one or more subsequent image processing steps, wherein the feature is a guidewire in the image.

In part, the disclosure relates to processor-based method of co-registering angiographic image data and intravascular image data obtained during a pullback through a blood vessel. The method includes storing a plurality of frames of optical coherence tomography data in memory; storing a plurality of frames of angiography image data in memory; processing the plurality of frames of angiography image data to generate a set of cross-frame co-registered angiography data; generating a vessel centerline for the plurality of frames of angiography image data; detecting a probe marker in the plurality of frames of angiography image data; tracking a position of the probe marker along one or more vessel centerlines; and co-registering the plurality of frames of angiography image data and the plurality of frames of optical coherence tomography data using the tracked position.

In one embodiment, the method further includes the step of generating a score indicative of a level of confidence in co-registration between a frame of angiography image data and a frame of the optical coherence tomography data. In one embodiment, the step of co-registering the plurality of frames of angiography image data and the plurality of frames of optical coherence tomography data comprises generating a co-registration table, using a computing device, the co-registration table comprising angiography image frames, a plurality of per frame OCT time stamps, a plurality of per frame angiography time stamps, and optical coherence tomography image frames including a score measurement for each co-registered position.

In one embodiment, the method further includes displaying a stent representation in an OCT image and an angiography image in a user interface using the co-registration table and a computing device. In one embodiment, the method further includes identifying a side branch in one or more OCT images or angiography images using the co-registration table and a user interface configured to display the side branch.

In one embodiment, x-ray image registration can be performed relative to one or more x-ray images as part of a cross-frame registration. Image registration can also be performed relative to or by using a representation of an arterial segment such as a section of a vascular tree. These representations can include a skeleton, a blood vessel or vascular tree coordinate or positional system, a geometric model of one or more blood vessels, and a curve or center line tracing a path through one or more blood vessels. These various representations can be detected, generated, or registered relative to one or more other images from another imaging modality such OCT, IVUS, or other intravascular imaging modalities.

Contrast Cloud Related Embodiments

In part, the disclosure relates to contrast cloud detection methods and diagnostic and analysis of angiography image frames that include one or more detected contract cloud regions.

In one aspect, the disclosure relates to a system of one or more computing devices can be configured to perform particular operations or actions by virtue of having software, firmware, hardware, software-based image processing modules or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a computing device-based method of detecting one or more regions of interest in one or more x-ray images, the method including: storing, in an electronic memory device, a set of angiography image frames obtained during a first time period that comprises one or more time periods during which contrast solution is in a blood vessel; detecting a plurality of candidate contrast cloud regions in one or more angiography frames; and combining the plurality of candidate contrast cloud regions to generate a fused contrast cloud region, the fused contrast cloud region having a cloud boundary. Other embodiments of this aspect include corresponding computer systems, apparatus, and computer programs recorded on one or more computer storage devices, each configured to perform the actions of the methods.

In various embodiments, implementations may include one or more of the following features. The method further includes excluding angiography image data located within the fused contrast cloud region from one or more subsequent data processing methods. In one embodiment, the one or more subsequent data processing methods includes generation of vessel centerlines. The method further includes generating one or more vessel centerlines for one or more angiography image frames. The method where the one or more subsequent data processing methods includes cross-frame registration of two or more angiography image frames of the set of angiography image frames. The method further includes performing cross-frame registration of two or more angiography image frames of the set of angiography image frames.

In one embodiment, the method further includes generating a set of cross-frame positions. The method where the one or more subsequent data processing methods includes a process selected from the group including of anchor point extraction; arc-length interpolation; and cross-frame position generation. The method further includes dilating one or more candidate regions or the fused contrast cloud region to provide an expanded exclusion zone and further includes excluding angiography image data located within the expanded exclusion zone from one or more subsequent data processing methods. The method further includes co-registering OCT image data and a plurality of the angiography image frames. The method further includes applying a smoothing filter to one or more angiography frames such that elements with a particular desired scale are preserved. The method further includes the step of adaptively thresholding a smoothed angiography frame with small-scale elements removed to generate a binary image, wherein one or more pixels in contrast cloud regions are a first value in the binary image.

In one embodiment, the method further includes the steps of selecting a contrast cloud neighborhood and overlaying the neighborhood on one or more angiography frames to include the cloud regions having the first value in the binary image. The method further includes the steps of counting or scoring number of pixels including the first value in the neighborhood. The method further includes the steps of adaptively thresholding pixels including first value and removing pixels from each neighborhood including a value other than the first value. The method further includes the step of generating a mask and using the mask to detect an anatomical stable anchor point to serve as a proximal end-point of a vessel centerline.

In one embodiment, the method further includes the step of detecting a plurality of anatomic features in the set of angiography image frames; generating clusters of the detected anatomic features and using the clusters to perform cross-frame registration between angiography frames, where a cluster refers to a single anatomic feature extracted from multiple frames. In one embodiment, the anatomic feature is a bifurcation or a bend point in a vascular tree.

In one embodiment, the method further includes the step of grouping a plurality of anatomically associated bend points using a shortest path-finding algorithm to identify a probable path through the associated bend points. The method wherein the probable path is identified in response to one or more criterion selected from the group including of bend angle change, curvature, curvature analog, bend position along a centerline, and bend angle deviations difference between consecutive frames. The method further includes the steps of applying an image processing transform to one or more frames to remove or modify a feature in at least one frame and generating a mask to perform feature extraction during one or more subsequent image processing steps, where the feature is a guidewire in the image.

In one embodiment, the method further includes co-registering the plurality of frames of angiography image data and the plurality of frames of optical coherence tomography data using a co-registration table, the co-registration table including angiography image frames, a plurality of per frame OCT time stamps, a plurality of per frame angiography time stamps, and optical coherence tomography image frames including a score measurement for each co-registered position. The method further includes displaying a stent representation in an OCT image and an angiography image in a user interface using the co-registration table and a computing device. The method further includes identifying a side branch in one or more OCT images or angiography images using the co-registration table and a user interface configured to display the side branch.

In one embodiment, the method further includes displaying a plurality of cross-frame registered angiography images using a diagnostic system, where the plurality of cross-frame registered angiography images is selected from the set.

The method wherein one or more steps of the method are implemented using a diagnostic system including an input to receive the set of frames from an angiography system, one or more electronic memory devices to store the set, one or more computing devices in electrical communication with the input and the one or more memory devices, and instructions, image filters and image processing software modules executable by the one or more computing devices to perform one or more steps of the method. Implementations of the described techniques may include hardware, a method or process, or computer software on a computer-accessible medium or be stored in a computer readable medium such as a non-transitory computer readable medium.

Guidewire Detection and Extraction Related Embodiments

In part, the disclosure relates to systems and methods to detect a guidewire in one or more frames of angiography data. In part, the disclosure relates to various diagnostic and image processing methods suitable for operating upon angiography images that include one or more guidewire segments.

In one embodiment, the disclosure relates to a system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions. One general aspect includes a processor-based method of detecting one or more regions of interest in one or more x-ray images, the method including: storing a set of angiography image frames obtained during a first time period in an electronic memory device; detecting a guidewire in one or more frames of the set; detecting arterial segments in one or more frames of the set; and generating a plurality of cross-frame positions with regard to a group of frames, the group of frames including:. The processor-based method of detecting one or more regions of interest also includes one or more frames including a detected guidewire. The processor-based method of detecting one or more regions of interest also includes one or more frames including one or more of the detected arterial segments. Other embodiments of this aspect include corresponding computer systems, apparatus, and computer programs recorded on one or more computer storage devices, each configured to perform the actions of the methods.

Implementations may include one or more of the following features. The method further includes. The method may also include performing arc length interpolation with regard to one or more detected arterial segments in one or more frames of the set. The method further includes performing cross-frame registration of the set of angiography image frames using the plurality of cross-frame positions. The method further includes identifying a plurality of anatomic features in one or more of the frames. The method wherein identifying an anatomic feature includes generating a cluster including a set of detected anatomic features across a plurality of frames, wherein the cluster is indicative of the detected anatomic feature being the same anatomic feature imaged at different times on different frames. The method further includes. The method may also include detecting a plurality of candidate contrast cloud regions in one or more angiography frames. The method further includes excluding regions of one or more of the angiography frames identified as including a contrast cloud region from a centerline generation process. The method further includes defining a proximal endpoint of one or more vessel centerlines using an endpoint selected from one or more of the candidate contrast cloud regions. The further including defining a distal endpoint of one or more vessel centerlines using an endpoint of a detected guidewire. The method further includes generating a plurality of vessel centerlines for a plurality of the angiography image frames in the set. The further including defining a distal endpoint of one or more vessel centerlines using an endpoint of a detected guidewire. The method further includes performing an intravascular data collection probe pullback during the first time period. The method wherein detecting a guidewire in one or more frames of the set includes.

In one embodiment, the method may also include applying a plurality of filters to an angiography image frame. The method may also include adaptively thresholding the filtered angiography frame. The method may also include operating on the adaptively thresholded angiography frame using an intensity filter to generate an intensity filtered frame. The method may also include detecting a guidewire portion in the intensity filtered frame. The method wherein the plurality of filters includes a morphological filter and a ridge enhancing filter. In one embodiment, the computing device includes further instructions to perform arc length interpolation with regard to one or more detected arterial segments in one or more frames of the set. In one embodiment, the computing device includes further instructions to perform cross-frame registration of the set of angiography image frames using the plurality of cross-frame positions.

In one embodiment, the computing device includes further instructions to detect a plurality of candidate contrast cloud regions in one or more angiography frames. In one embodiment, the computing device includes further instructions to define a proximal endpoint of one or more vessel centerlines using an endpoint selected from one or more of the candidate contrast cloud regions. In one embodiment, the computing device includes further instructions to define a distal endpoint of one or more vessel centerlines using an endpoint of a detected guidewire. In one embodiment, the computing device includes further instructions to generate a plurality of vessel centerlines for a plurality of the angiography image frames in the set. In one embodiment, the computing device includes further instructions to define a distal endpoint of one or more vessel centerlines using an endpoint of a detected guidewire. In one embodiment, the computing device includes further instructions such that detecting a guidewire in one or more frames of the set includes applying a plurality of filters to an angiography image frame. The system may also include adaptively thresholding the filtered angiography frame. The system may also include operating on the adaptively thresholded angiography frame using an intensity filter to generate an intensity filtered frame. The system may also include detecting a guidewire portion in the intensity filtered frame. In one embodiment, the plurality of filters includes a morphological filter and a ridge enhancing filter. Implementations of the described techniques may include hardware, a method or process, or computer software on a computer-accessible medium.

One general aspect includes a system for detecting one or more features in an angiographic image, the system including: one or more memory devices; and a computing device in communication with the memory device, wherein the memory device includes instructions executable by the computing device to cause the computing device to: store a set of angiography image frames obtained during a first time period in an electronic memory device; detect a guidewire in one or more frames of the set; detect arterial segments in one or more frames of the set; and generate a plurality of cross-frame positions with regard to a group of frames. The system also includes one or more frames including a detected guidewire. The system also includes one or more frames including one or more of the detected arterial segments. Other embodiments of this aspect include corresponding computer systems, apparatus, and computer programs recorded on one or more computer storage devices, each configured to perform the actions of the methods.

Implementations may include one or more of the following features. In one embodiment, the computing device includes further instructions to perform arc length interpolation with regard to one or more detected arterial segments in one or more frames of the set. In one embodiment, the computing device includes further instructions to as recited herein. The system may also include perform cross-frame registration of the set of angiography image frames using the plurality of cross-frame positions. In one embodiment, the computing device includes further instructions to detect a plurality of candidate contrast cloud regions in one or more angiography frames.

In one embodiment, the computing device includes further instructions to define a proximal endpoint of one or more vessel centerlines using an endpoint selected from one or more of the candidate contrast cloud regions. In one embodiment, the computing device includes further instructions to define a distal endpoint of one or more vessel centerlines using an endpoint of a detected guidewire. In one embodiment, the computing device includes further instructions to generate a plurality of vessel centerlines for a plurality of the angiography image frames in the set. In one embodiment, the computing device includes further instructions to define a distal endpoint of one or more vessel centerlines using an endpoint of a detected guidewire.

In one embodiment, the computing device includes further instructions such that detecting a guidewire in one or more frames of the set includes. The system may also include applying a plurality of filters to an angiography image frame. The system may also include adaptively thresholding the filtered angiography frame. The system may also include operating on the adaptively thresholded angiography frame using an intensity filter to generate an intensity filtered frame. The system may also include detecting a guidewire portion in the intensity filtered frame. In one embodiment, the plurality of filters includes a morphological filter and a ridge enhancing filter. Implementations of the described techniques may include hardware, a method or process, or computer software on a computer-accessible medium.

Anatomic Feature Detection Embodiments

In part, the disclosure relates to anatomic feature detection and clustering based validation methods. In one aspect, the disclosure relates to processor-based method of detecting one or more regions of interest in one or more x-ray images. The method includes storing a set of angiography image frames obtained during a first time period in an electronic memory device; generating a plurality of centerlines for a plurality of the angiography image frames generating a binary image of an angiography image frame, for a group of angiography image frames; and generating a skeleton images from the binary images.

In one embodiment, the method includes applying a rib filter or a temporal filter to the skeleton images. In one embodiment, the method includes detecting one or more anatomical features in the skeleton images. In one embodiment, the method includes detecting one or more anatomical features in the filtered skeleton images. In one embodiment, the anatomical features are a plurality of bifurcation. In one embodiment, the anatomical features are a plurality of bend points. In one embodiment, the method includes detecting an anatomic feature comprises generating a cluster comprising a set of detected anatomic features across a plurality of frames, wherein the cluster is indicative of the detected anatomic feature being the same anatomic feature imaged at different times on different frames. In one embodiment, the method includes g applying a vessel crossing filter to the skeleton images. In one embodiment, the skeleton images are generated from the vessel centerlines. In one embodiment, the method includes generating a plurality of clusters, wherein each cluster is a single anatomical feature extracted from a group of frames. In one embodiment, the method includes generating one or more distance measurements between two or more clusters.

In one embodiment, the distance metric is a Euclidean metric. In one embodiment, the method includes validating an anatomical feature as a result of it being present on two or more angiography image frames. In one embodiment, the method includes consolidating the clusters to generates a set of clusters each having a single representative from each frame of interest. In one embodiment, the method includes selecting one or more clusters. In one embodiment, the clusters are selected based on a parameters selected from the group consisting of: arc-length standard deviation, normalized arc-length standard deviation, angle difference standard deviation, proximity to other clusters, average number of redundant anatomical feature records per frames, and average number of missing bifurcation records per frame.

Although, the invention relates to different aspects and embodiments, it is understood that the different aspects and embodiments disclosed herein can be integrated together as a whole or in part, as appropriate. Thus, each embodiment disclosed herein can be incorporated in each of the aspects to varying degrees as appropriate for a given implementation and steps from various methods can be combined without limitation.

Other features and advantages of the disclosed embodiments will be apparent from the following description and accompanying drawings.

BRIEF DESCRIPTION OF DRAWINGS

The figures are not necessarily to scale; emphasis instead is generally being placed upon illustrative principles. The figures are to be considered illustrative in all aspects and are not intended to limit the disclosure, the scope of which is defined only by the claims.

FIG. 15B and 15C are an original angiography image and skeleton of one of the main vessels in that image, respectfully, after the application of image processing and data analysis in accordance with an illustrative embodiment of the disclosure.

DETAILED DESCRIPTION

Figure 1:
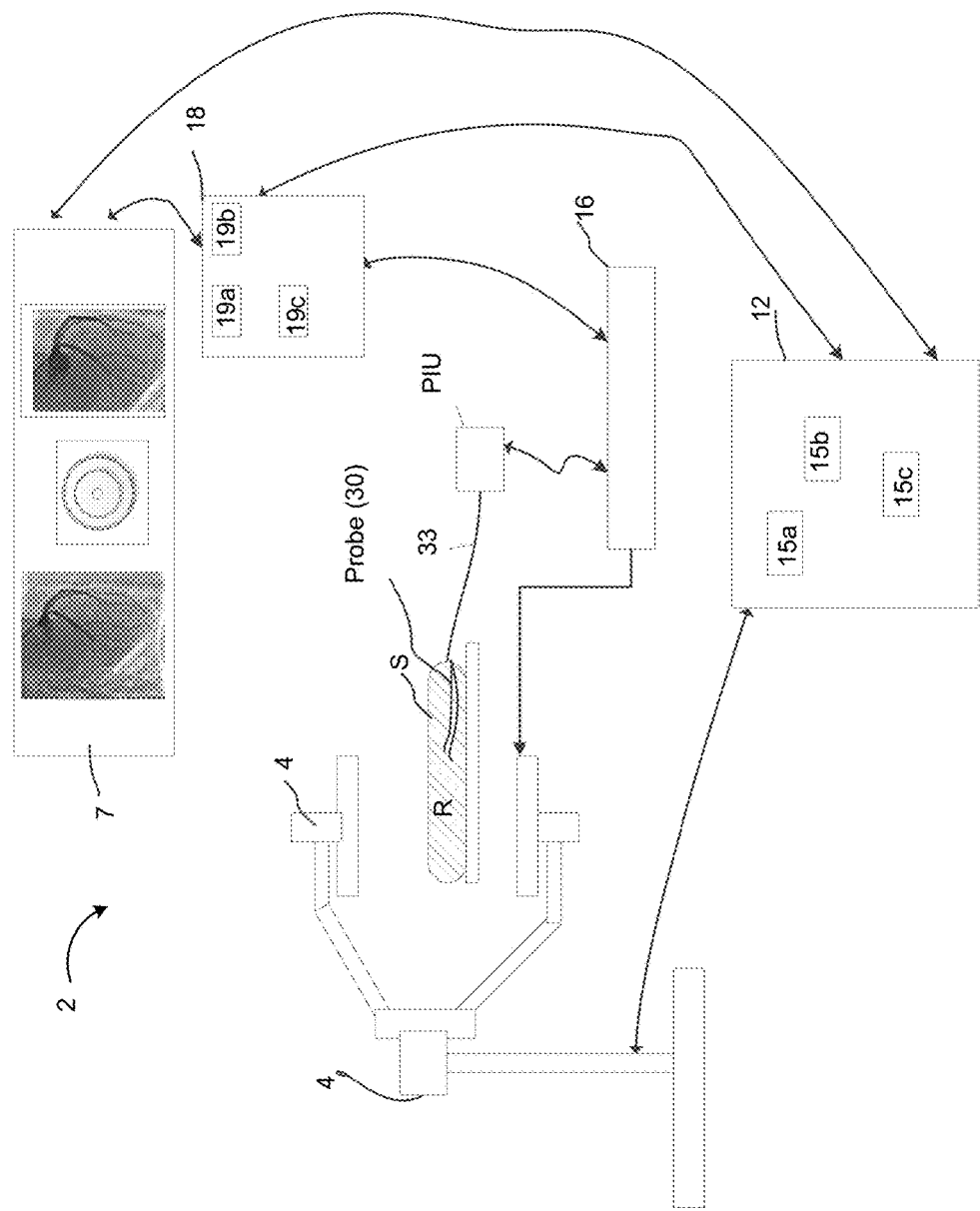
FIG. 1 is a schematic diagram of an x-ray-based imaging system and intravascular imaging and data collection system in accordance with an illustrative embodiment of the disclosure.

The disclosure relates to various methods, systems, and apparatus relating to x-ray imaging such as angiography and its application to cardiology. In particular, the disclosure relates to co-registering features with regard to frames of angiography data across or between such frames. The disclosure also relates to various methods to improve such co-registration such as by reducing errors or detecting structures associated with frames of angiography data.

As an example of such error reducing methods and other angiography or peripheral vascular system imaging enhancements, several are discussed in detail herein. These embodiments relate to contrast cloud detection, extracting or identifying wires in frames of x-ray image data and tracking or registering features and devices relative to the vascular system including with respect to angled branches and bifurcations or guidewires. These embodiments reduce errors that can propagate through other registration processes and lead to additional errors and inaccuracies. Ultimately, such errors can preclude proper cross-frame registration between angiography frames and any co-registration of other imaging modalities with such angiography frames. The errors can also interfere with tracking and co-registering probe movements for probes that include one or more markers such as radiopaque markers.

Interventional cardiologists use fluoroscopy combined with contrast injection as for angiography imaging. The contrast spreads through the vascular trees and allows them to be viewed via x-ray. Typically, a time varying contrast cloud is formed near the catheter tip. The locus or point of delivery of the contrast solution is highly variable with a blob or cloud like shape. This high varying structure might hide underlying anatomical information and disturb various image processing and computer vision algorithms such as tracking and object or feature detection. The cloud can have various lobes or regions with irregular shapes. As a result, an OR or other combination or union operator can be used to combine various detected regions and aggregate them or define them with an envelope or border to define the overall cloud region. In one embodiment, the contrast cloud defines a region of data exclusion defined by a union of various regions or neighborhoods that are determined to be contrast-containing regions.

The presence of a contrast cloud itself can generate unwanted imaging artifacts and errors. Similarly, the presence of one or more guidewires in the artery during imaging can result in imaging errors and misinterpretation of the guidewire. In addition, the tortuous and overlapping nature of the vascular system itself can make it difficult to track where a given intravascular probe or other medical device is positioned relative to angiography frames of data. Also, it is difficult for a human viewer and for an automated diagnostic system to determine which displayed segments of vessels in frames of angiography data correspond to and align with the twists and turns and overlapping sections of the vascular system with its various side branches and pathways. Some of the methods and systems described herein facilitate solutions to these challenges. In light of the foregoing, in part, the disclosure relates to a method for detecting the location and extent of contrast clouds generated during contrast enhanced x-ray scans, for example, x-ray angiography.

In addition, during various treatments, diagnostic and intravascular imaging techniques various wires can be used to guide catheters, balloons, stents, or other devices. As part of the display of information to a user as part of a diagnostic and intravascular imaging techniques, the disclosure relates to methods to determine the location of the wire and/or the wire tip from frames of data such as angiography frames. In turn, this information can be used to support and enhance the user's viewing and interpretation of x-ray and intravascular images of the vasculature. The vascular system includes various tortuous pathways that trace the different side branches and arteries. As a result, the disclosure also describes methods for registration of vascular trees in sequences of x-ray images. In this way, some of the guesswork out of how overlapping arterial branches in an x-ray correspond to a three-dimensional tree of branches that need to be navigated and interpreted as they change and move from frame to frame in response to heart beats or other phenomena. The foregoing features help enhance the accuracy of cross-frame registration by addressing factors which can cause registration errors.

These categories of embodiments and the others described herein can be used in various x-ray imaging systems including those that work in concert with optical coherent tomography, ultrasound, or other imaging and data collection systems. Intravascular imaging technologies are valuable tools that can be used in lieu of or in combination with fluoroscopy or other x-ray imaging systems. By looking within a blood vessel, these imaging technologies can obtain high-resolution data regarding the condition of the blood vessels for a given subject. Combing these intravascular images with cross-frame registered angiography images obtained during the intravascular imaging and solving some of the challenges of contrast cloud noise, overlapping branches, and guidewire artifacts directly improves diagnostic accuracy.

As a result, intravascular imaging technologies such as optical coherence tomography (OCT) and acoustic technologies such as intravascular ultrasound (IVUS) and others are also described herein. For example, such blood vessel imaging is used by physicians to diagnose, locate and treat blood vessel disease during interventions such as bypass surgery or stent placement. FIG. 1 shows an exemplary system 2 for implementing one or more embodiments of the invention that includes an x-ray imaging system 4 such as an angiography system.

The data collection system 2 includes a noninvasive imaging system such as a nuclear magnetic resonance, x-ray, computer aided tomography, or other suitable noninvasive imaging technology indicated by system 4. As shown as a non-limiting example of such a noninvasive imaging system, an angiography system 4 such as suitable for generating cines is shown. The angiography system 4 can include a fluoroscopy system. Angiography system 4 is configured to noninvasively image the subject S such that frames of angiography data, typically in the form of frames of image data, are generated. This x-ray imaging occurs while a pullback procedure is performed using a probe such that a blood vessel in region R of subject S is imaged using angiography and one or more imaging technologies such as OCT or IVUS, for example. The imaging results of a non-invasive scan (left and right images in display 7) and intravascular imaging results such as from OCT or IVUS are shown in the middle panel of display 7. In addition to the display, the probe used to collect intravascular data can be disposable and connect to a patient interface unit or PIU as part of system 2.

The angiography system 4 is in communication with an angiography data storage and image management system 12, which can be implemented as a workstation or server in one embodiment. In one embodiment, the data processing relating to the collected angiography signal is performed directly on the detector of the angiography system 4. The images from system 4 are stored and managed by the angiography data storage and image management 12. In one embodiment, a subsystem, a server or workstation handle the functions of system 12. In one embodiment, the entire system 4 generates electromagnetic radiation, such as x-rays. The system 4 also receives such radiation after passing through the subject S. In turn, the data processing system 12 uses the signals from the angiography system 4 to image one or more regions of the subject S including region R. In one embodiment, system 12 and an intravascular system 18 are all part of one integrated system.

As shown in this particular example, the region of interest R is a subset of the vascular or peripherally vascular system such as a particular blood vessel. This region R can be imaged using OCT or another intravascular modality. A catheter-based data collection probe 30 is introduced into the subject 10 and is disposed in the lumen of the particular blood vessel, such as for example, a coronary artery. The probe 30 can be a variety of types of data collection probes such as for example an OCT probe, an FFR probe, an IVUS probe, a probe combining features of two or more of the foregoing, and other probes suitable for imaging within a blood vessel. The probe 30 typically includes a probe tip, one or more radiopaque markers, an optical fiber, and a torque wire. Additionally, the probe tip includes one or more data collecting subsystems such as an optical beam director, an acoustic beam director, a pressure detector sensor, other transducers or detectors, and combinations of the foregoing.

For a probe that includes an optical beam director, the optical fiber 33 is in optical communication with the probe with the beam director. The torque wire defines a bore in which an optical fiber is disposed. In FIG. 1, the optical fiber 33 is shown without a torque wire surrounding it. In addition, the probe 30 also includes the sheath such as a polymer sheath (not shown) which forms part of a catheter. The optical fiber 33, which in the context of an OCT system is a portion of the sample arm of an interferometer, is optically coupled to a patient interface unit (PIU) as shown.

The patient interface unit PIU includes a probe connector suitable to receive an end of the probe 30 and be optically coupled thereto. Typically, the data collection probes 30 are disposable. The PIU includes suitable joints and elements based on the type of data collection probe being used.

For example, a combination OCT and IVUS data collection probe requires an OCT and IVUS PIU. The PIU typically also includes a motor suitable for pulling back the torque wire, sheath, and optical fiber 33 disposed therein as part of the pullback procedure. In addition to being pulled back, the probe tip is also typically rotated by the PIU. In this way, a blood vessel of the subject 10 can be imaged longitudinally or via cross-sections. The probe 30 can also be used to measure a particular parameter such as an FFR or other pressure measurement.

In turn, the PIU is connected to one or more intravascular data collection systems 18. The intravascular data collection system 18 can be an OCT system, an IVUS system, another imaging system, and combinations of the foregoing. For example, the system 18 in the context of probe 30 being an OCT probe can include the sample arm of an interferometer, the reference arm of an interferometer, photodiodes, a control system, and patient interface unit. Similarly, as another example, in the context of an IVUS system, the intravascular data collection system 18 can include ultrasound signal generating and processing circuitry, noise filters, rotatable joint, motors, and interface units.

In one embodiment, the data collection system 18 and the angiography system 4 have a shared clock or other timing signals configured to synchronize angiography video frame time stamps and OCT image frame time stamps. In one embodiment, angiography system 12 runs various image processing and feature detection and other software-based processes as shown by 15a, 15b and 15c. In one embodiment, angiography system 12 runs various image processing and feature detection and other software-based processes as shown by 15a, 15b and 15c. These processes can include contrast cloud detection processes, feature extraction processes, wire detection and feature extraction relative thereto, interframe registration processes, cross frame registration process and other processes, methods and steps as described herein.

In general, software-based processes 15a, 15b and 15c are designed to reduce errors in cross-frame registration and to perform other processes described herein such as detecting a feature in an x-ray image and flagging it for use or exclusion in subsequent processing steps. Thus, a contrast cloud can be detected and then flagged by such software processes so that the region of the cloud is not used for processes that will be negatively impacted by the positional uncertainty and noise in the region.

In embodiment, it is advantageous that the contrast cloud is located near the proximal end-point of a vessel being imaged via x-rays. As part of the process of determining centerlines, a contrast cloud location can be used to select an endpoint to help select a centerline endpoint from a set of candidate endpoints or define a given centerline endpoint. In embodiment, it is advantageous that the guidewire is located near the distal end-point of a vessel being imaged via x-rays. As part of the process of determining centerlines, a guidewire location can be used to select an endpoint to help select a centerline endpoint from a set of candidate endpoints or define a given centerline endpoint.

The disclosure can be realized as one or more computer program products, i.e., one or more modules of computer program instructions encoded on a computer readable medium for execution by, or to control the operation of, a data processing apparatus. The computer readable medium can be a machine-readable storage device, a machine-readable storage substrate, a memory device, or a combination of one or more of them. The term "data processing apparatus" encompasses all apparatus, devices, and machines for processing data, including by way of example a programmable processor, a computing device such as a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this disclosure can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read-only memory or a random-access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices.

A computer or computing device can include machine readable medium or other memory that includes one or more software modules for displaying a graphical user interface such as interface. A computing device can exchange data such as monitoring data or other data using a network, which can include one, or more wired, optical, wireless or other data exchange connections.

A computing device or computer may include a server computer, a client user computer, a control system, an intravascular or angiography diagnostic system, a microprocessor or any computing device capable of executing a set of instructions (sequential or otherwise) that specify actions to be taken by that computing device. Further, the term "computing device" shall also be taken to include any collection of computing devices that individually or jointly execute a set (or multiple sets) of instructions to perform any one or more of the software features or methods or operates as one of the system components described herein.

In addition to the invasive and noninvasive image data collection systems and devices of FIG. 1, various other types of data can be collected with regard to region R of the subject and other parameters of interest of the subject. This can include positional information, vessel diameters, vessel bifurcation locations, regions and neighborhoods of pixel intensity variations and other data, The data collection system 2 can include one or more displays 7 to show angiography frames of data, an OCT frames, user interfaces for OCT and angiography data. The co-registration of angiography frames relative other angiography frames allows. The displays 7 can also show other controls and features of interest.

The noninvasive image data generated using angiography image analysis and processing system 12 can be transmitted to, stored in, and processed by one or more servers or workstations which can be system 12 or system 18 as shown in FIG. 1. Intravascular image processing system 16 can be in electrical communication with the PIU and an image processing subsystem 18. The subsystem 18 includes various software modules to track marker positions and perform co-registration between intravascular image frames and x-ray image frames. The intravascular image data such as the frames of intravascular data generated using the data collection probe 30 can be routed to the data collection processing system 45 coupled to the probe via PIU 35. A video frame grabber device such as a computer board configured to capture the angiography image data from system 12 can be used in various embodiments.

Figure 2A:
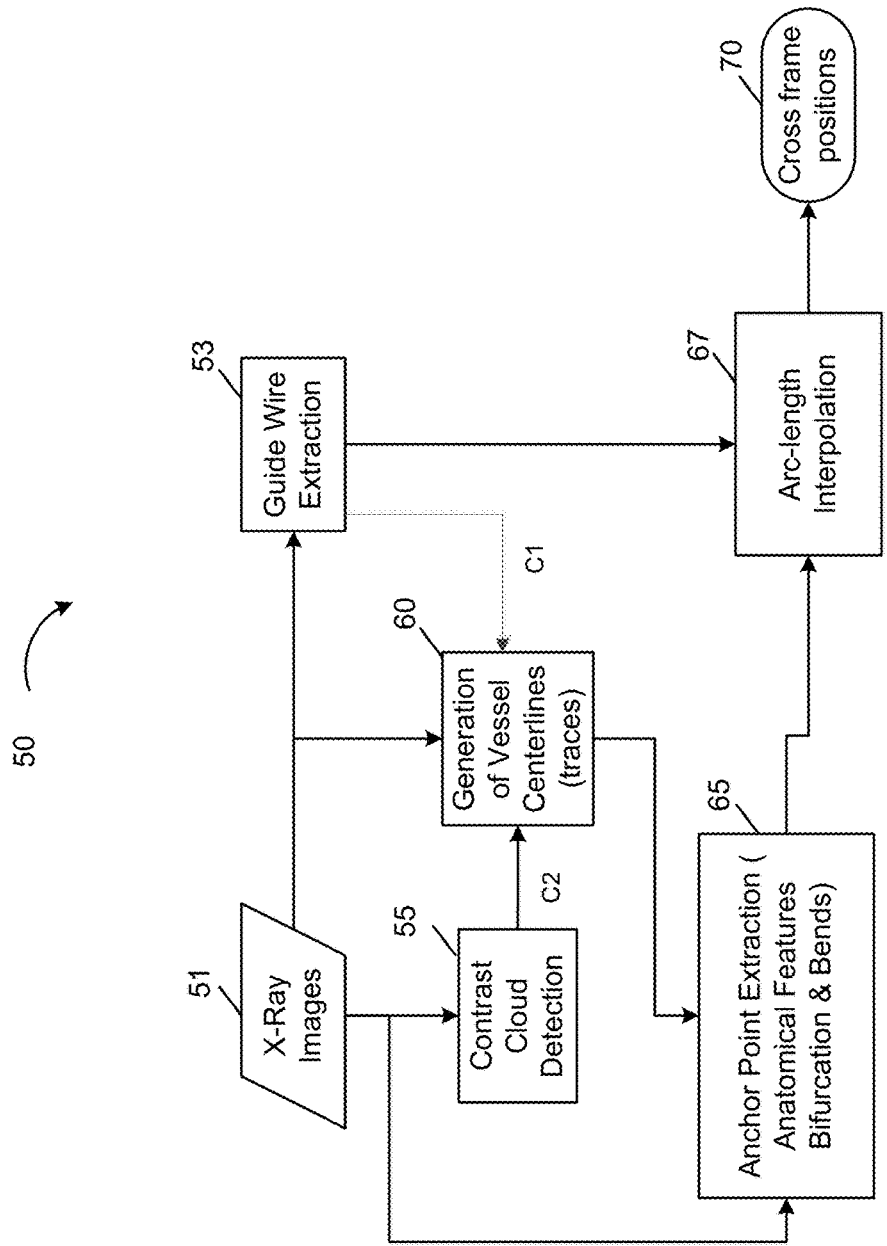
FIG. 2A is a schematic diagram of an angiography image processing and frame tracking system and components there of suitable for co-registering x-ray images with intravascular images by generating a plurality of cross-frame positions in accordance with an illustrative embodiment of the disclosure.

As shown FIG. 2A, as part of an overall architecture of stages and process flow 50 a sequence of x-ray images 51 is generated as the output of angiography system 4 and transmitted to data collection system 12 for image processing and storage. In one embodiment, the x-rays are obtained during pullback intravascular probe through an artery. Each artery is part of the vascular system and may connect to various junctions or bifurcations as well as one or more side branches. These branches and bifurcations may diverge at various angles from the section of the artery of interest such as an artery simultaneously undergoing a pullback imaging procedure using OCT or IVUS. Guide wire extraction subsystem and methods 53 can operate upon and transform the x-rays to remove the appearance of the guidewire used to position probe 30 in a given image frame. The location and terminal end points and other points along the detected guidewire can also be evaluated and used as anchor points as part of other image and data processing and analysis as described herein. In one embodiment, as used herein references to "extraction" can also be considered as referring to "detection" or "determination" and vice versa.

As discussed herein imaging of such an artery is enhanced by the introduction of radiopaque contrast solution. A contrast cloud is created that is visible as a region on individual frames of x-ray images. This cloud is formed in the vicinity of where the contrast solution is introduced. The data collection system includes a contrast cloud detection subsystem and/or method 55 that operates on x-ray image frames to characterize and/or detect the contrast cloud and regions thereof. This subsystem can be implemented in software modules 15a, 15b, or 15c or combinations thereof as part of system 12. The contrast cloud detection methods 55 can be implemented using one or more software components that operate upon and transform x-ray images such as by detecting features thereon or increasing or decreasing image properties of a given frame. The various flow charts, stages and processes shown in FIG. 2A and as otherwise described herein can be performed using the intravascular and angiography systems and other computing devices and diagnostic control systems and processors as described herein.

In addition to performing detection and image processing steps to identify and exclude problematic contrast containing regions of an angiography frame, the disclosure also includes processing stages and software-based methods relating to generating vessel centerlines 60. Centerline generation can be enhanced as a result of the exclusion of contrast cloud regions. Once the centerlines are generated an anchor point extraction stage and/or methods 65 can be used to detect any suitable anatomic feature in an x-ray image, such as for example bifurcations and bends. These features can be used for various diagnostic and image processing methods. In one embodiment, once feature extraction has been performed relative to these structures, clusters and groups of per frame representative anatomic features such as, for example, bifurcations and bends can be used to reduce co-registration errors and low confidence scores.

As a result, the accuracy between which angiography frame is shown on the display relative to the intravascular image frame with respect to which it is to be co-registered or registered on a cross-frame basis increases. The co-registration and cross-frame registration process facilitates diagnostic review, stent deployment review, and stent planning. As a result, reducing registration errors through the contrast cloud detection, guidewire extraction and detection of bifurcations and bends is important to achieving accurate co-registration and diagnose the arterial state or stent state by an end user. In various embodiments, registration includes co-registration and cross-frame registration and vice versa. In one embodiment, the contrast cloud detection process 55 and the guidewire extraction process 53 can generate positional values for defining a centerline endpoint. For example, a first centerline endpoint value C1 and a second centerline endpoint value C2 can be generated from contrast cloud detection 55 and guidewire extraction 53, respectively, or vice versa. The generation of proximal and distal endpoint values for a centerline using contrast cloud detection data and guidewire detection data enhances centerline confidence and reduces additional levels of computation as a result of using angiography image data to inform the terminal location of a given centerline.

Figures 2B, 2C:
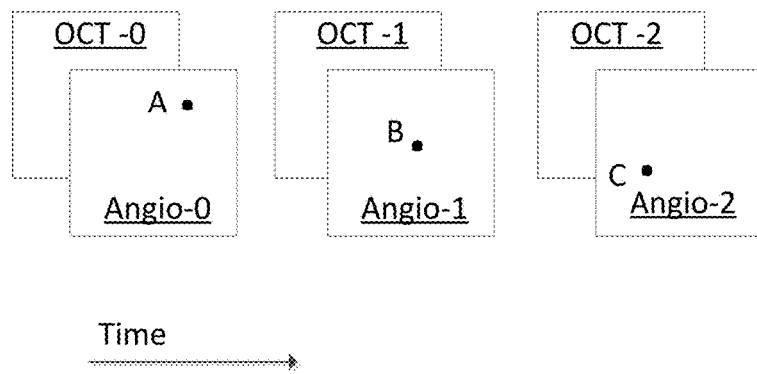
FIG. 2B is an exemplary co-registration table that includes various parameters and outputs from performing imaging using an x-ray system during an OCT or other intravascular pullback to perform co-registration between frames in accordance with an illustrative embodiment of the disclosure.
FIG. 2C is a schematic diagram of three OCT image frames and the corresponding three angiography image frames obtained during a pullback of an OCT probe having a radiopaque marker through an artery in accordance with an illustrative embodiment of the disclosure.

As shown in FIG. 2A, arc-length interpolation stage and related steps 67 can be performed with the detected anchor points such that any anatomical landmarks or features that can be detected on the x-ray images and used to identify corresponding vessel segments in all angiography frames. In one embodiment, the anatomical landmarks or features includes bifurcations, bends, as one or more of bifurcations and bend information to identify corresponding vessel segments in all angiography frames. By using the arc-length based interpolation, the cross-frame positions can be generated. The cross-frame positions facilitate tracking the position of a probe's radiopaque marker across angiography frames. The marker is moving element which transitions through different points during a pullback as shown in FIG. 2C. For example, these positions can be tracked relative to anatomical features or other landmarks in the angiography frames. In one embodiment, the tracking of these positions is combined with the tracking of the radio-opaque marker to perform co-registration the intravascular imaging data.

FIG. 2B shows a co-registration table that is generated by one or more of the systems of FIG. 1 after the angiography frames have undergone cross-frame co-registration. That is, co-registration between different angiography frames. The table of FIG. 2A show different times for the OCT and angiography frames because they typically operate on different system or data sampling clocks or time periods. The (x,y) position of the probe marker on each frame is displayed in the table. A score, which is a measure of the confidence of registration between angiography frames and OCT frames, is also shown. The angio index is the frame number for the angiography sequence of images. FIG. 2C shows a schematic representation of the marker on the probe moving to different (x,y) spatial positions over time and which OCT frames correspond to the associated angiography frames. The marker moves through positions A, B, and C in each of the three intravascular image frames (OCT-0, OCT-1, and OCT-2) and the three angiography frames (Angio-0, Angio-1, and Angio-2) and can be registered on a cross frame basis between frames.

Contrast Cloud Feature Extraction/Detection Related Methods and Analysis

In part, the disclosure relates to methods to improve the tracking accuracy of the proximal vascular end point, which typically is located and disturbed by its proximity to the contrast cloud. Detection of the contrast cloud allows for improvement of the stabilization of the proximal vascular end points in OCT-angiography co-registration. Specifically, the presence of a contrast cloud complicates OCT-angiography co-registration and cross-frame registration between x-ray frames such as creating uncertainty when determining centerlines that have end-points which maintain their anatomical position across the angiography frame set.

During x-ray guided procedures, physicians use x-ray scans combined with contrast agents to visualize blood vessels and cardiac chambers. During contrast injection, a contrast cloud can form near the contrast-leading catheter. The contrast cloud is typically amorphic and varies in shape and size in different image frames collected during a scan. A contrast cloud has the potential to block or hide underlying structures and potentially lead to decreased performance of various image processing and computer vision algorithms. Detecting the location and extent of a contrast cloud from a single or multiple image frames establish a refined region of interest when applying image processing and computer vision algorithms.

For other purposes, it may also be used as an image landmark. Essentially, the regions of detected contrast cloud can be flagged as noisy or indeterminate regions with respect to which positional data and other image information used for other subsequent image and data processing is excluded. This follows because data from such a noisy or indeterminate region can introduce errors which propagate through other subsequent image data transformations which in turn cause additional errors and registration inaccuracies.

A contrast cloud detector can be utilized to produce a binary image in which the bright components of the binary image are the regions of the image that contain cloud regions. Alternatively, bright regions can be inverted and dark regions can be used for cloud detection in other embodiments. In one exemplary embodiment, a fused mask can be generated from binary images from a plurality of image frames, and can be generated using a variety of techniques, including the use of a pixel wise OR operation.

A post filtering stage can be used to remove small component or components that are out of the region of interest. These cloud regions or summed or OR'd combination of cloud regions define a region to be excluded such that marker tracking is not performed in such regions or subsets thereof. These cloud regions can also be excluded from cross-frame processes, centerline generation, and other processes as described herein. The OR'd combination follows from performing an OR operation that combines cloud regions into an aggregated or fused cloud region. In this way, multiple candidate cloud regions can be combined to increase the chances of properly excluding regions where the contrast cloud is likely to be present. These regions, if used, would be a source of error and marker position uncertainty which would have a deleterious effect on subsequent processing steps.

Thus, in one embodiment when tracking the opaque marker of an imaging probe relative to the x-ray image frames generated using system 4 the regions identified as containing contrast cloud are excluded such that marker tracking is not performed therein. The same exclusion applies to the other detections and processes described herein. Contrast cloud regions in an image can also be excluded from cross-frame analysis. By detecting the contrast cloud and defining a region associated with it, anatomical positions near or on the contrast cloud can be tracked with higher accuracy.

In addition, the boundary or end of the detected contrast cloud provides a basis for identifying which frames can be used to start other processes such as registration processes or other processes as described herein. As a result, for example, greater tracking accuracy improves vessel centerline determination and thus improves the accuracy achieved when determining cross-frame positions. This reduces imaging artifacts and misalignment between vessel segments after a co-registration process is performed such as by generating a co-registration table such as that shown in FIG. 2B.

Figure 3:
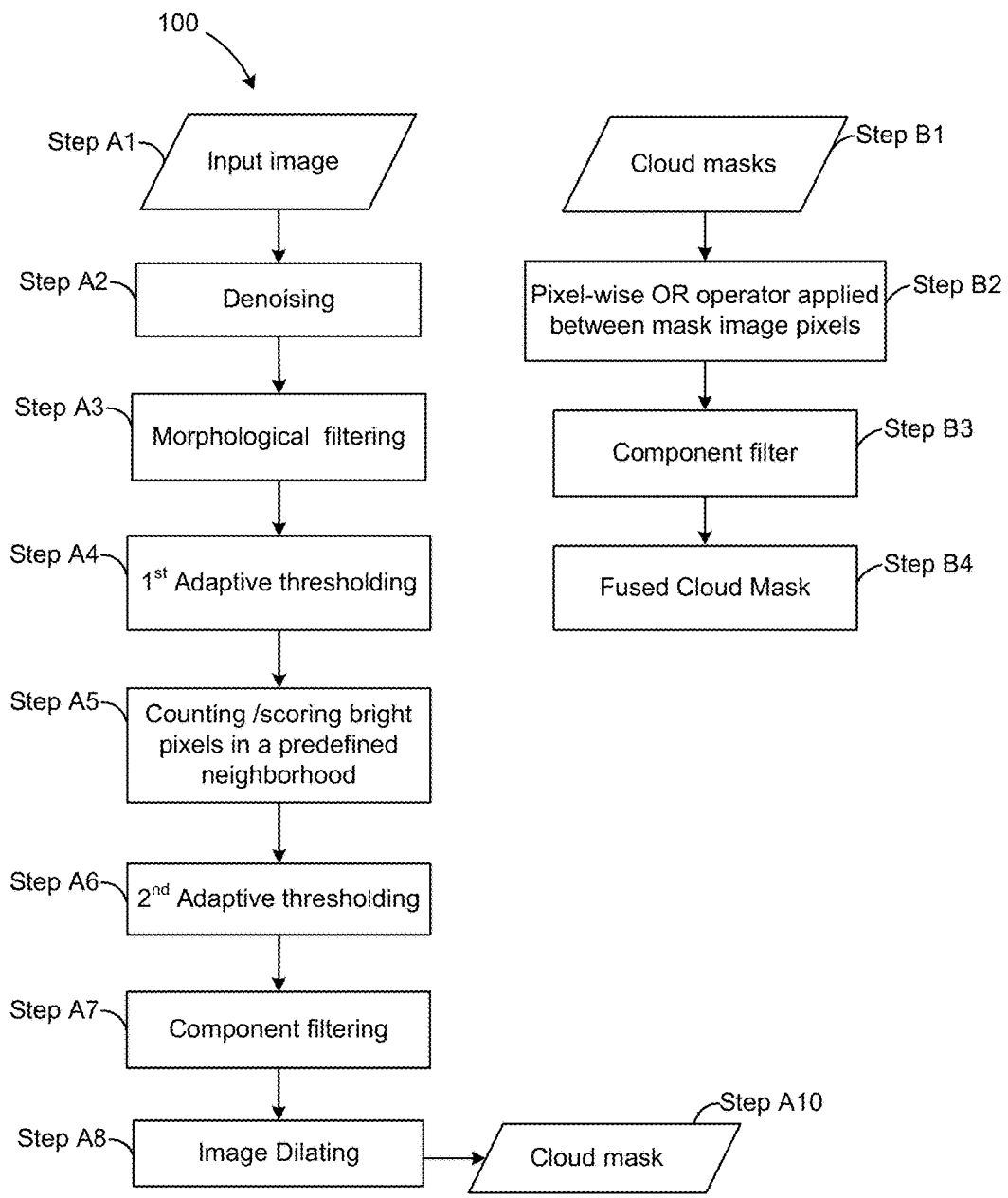
FIG. 3 is a flowchart illustrating a method of detecting a contrast cloud in one or more x-ray images generated by the injection of a contrast agent into a vessel in accordance with an illustrative embodiment of the disclosure.
Figure 4:
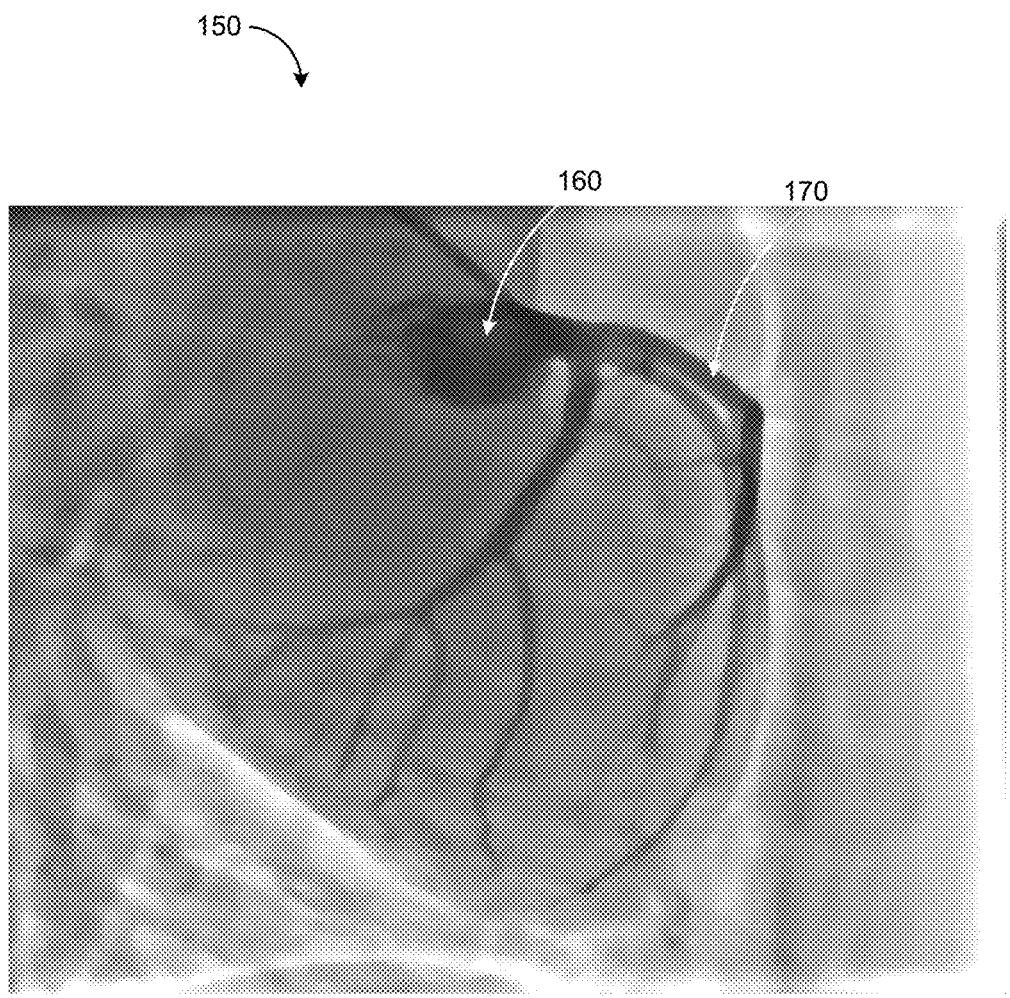
FIG. 4 is an x-ray image frame of a blood vessel with a contrast agent injected therein after a de-noising process was applied to the image frame in accordance with an illustrative embodiment of the disclosure.

FIG. 3 illustrates a flowchart 100 of a method for detecting a contrast cloud for each input image. In step A1, an image is input into a system for processing for the detection of a contrast cloud. In step A2, the image is denoised to produce a smoother image. This step can be an optional step, but can improve the image and can be important for noisy x-ray images. If the image is one of better quality, step A2 can be skipped. FIG. 4 illustrates an exemplary image of an x-ray image 150 of a vessel 170 with a contrast agent 160 region after image denoising has been performed. Knowing the location of cloud 160 allows the improvement of the consistency and stability of vessel centerlines which leads to improved accuracy of the co-registration and tracking of the marker of the probe.

Figure 5:
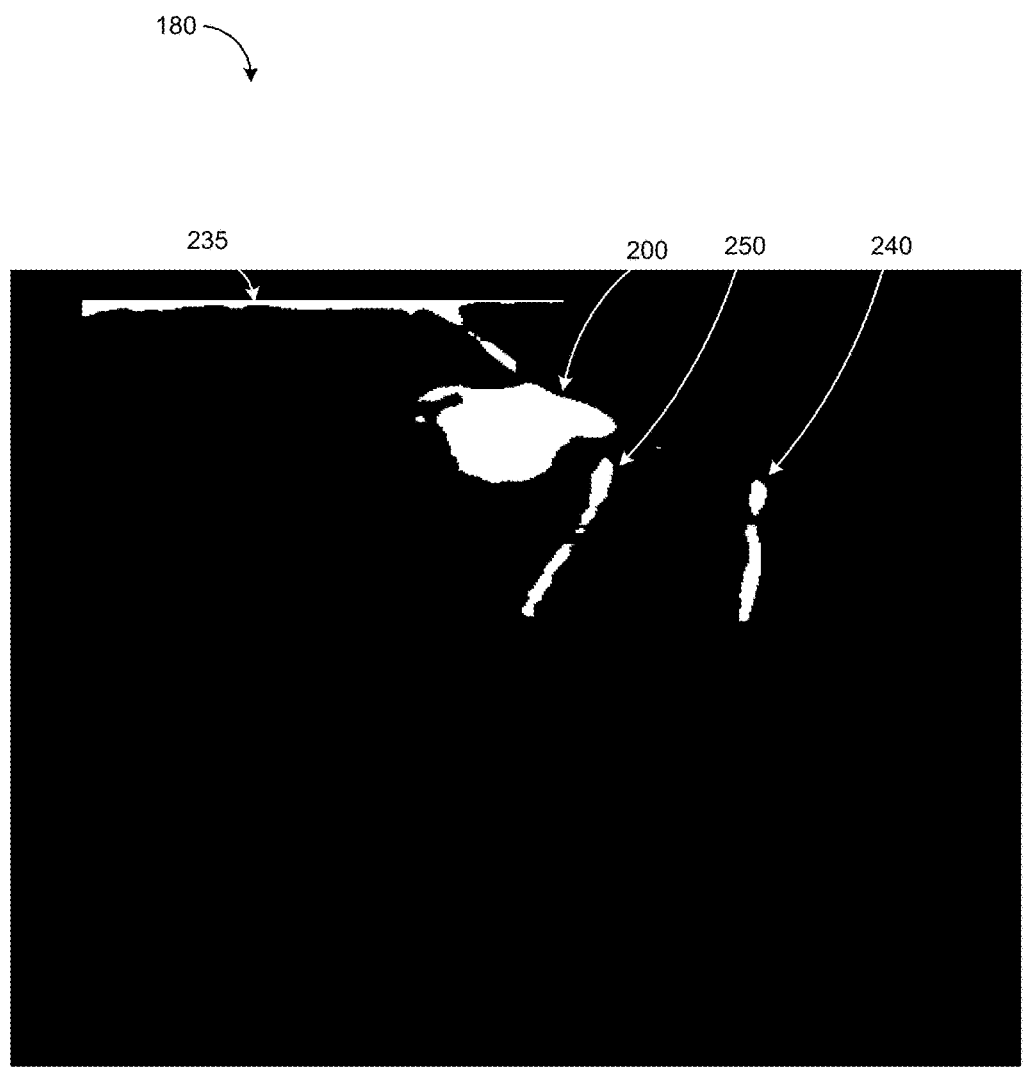
FIG. 5 is a view of an exemplary binary image of a contrast cloud after adaptive thresholding has been applied to an x-ray image frame of a vessel in accordance with an illustrative embodiment of the disclosure.

In step A3, optionally, a morphological filter is applied to the image to smooth and improve cloud homogeneousness in terms of intensity and shape (by decreasing the number of gaps). In one embodiment, step A2 and A3 can be combined in a general denoising step. In one embodiment, step A2 and A3 are both optical. In step A4, a first adaptive thresholding is used on the image to produce a binary image. FIG. 5 illustrates an exemplary image in which adaptive thresholding is used to produce a binary image 180. As seen in FIG. 5, the pixels, or portions, of the image of FIG. 4 that were darker regions, including the area of the potential contrast cloud, are represented by bright white regions 200, 235, 240, 250 in the binary image 180 of FIG. 5. In FIG. 5, a binary image after adaptive thresholding has been performed is shown.

Figure 6:
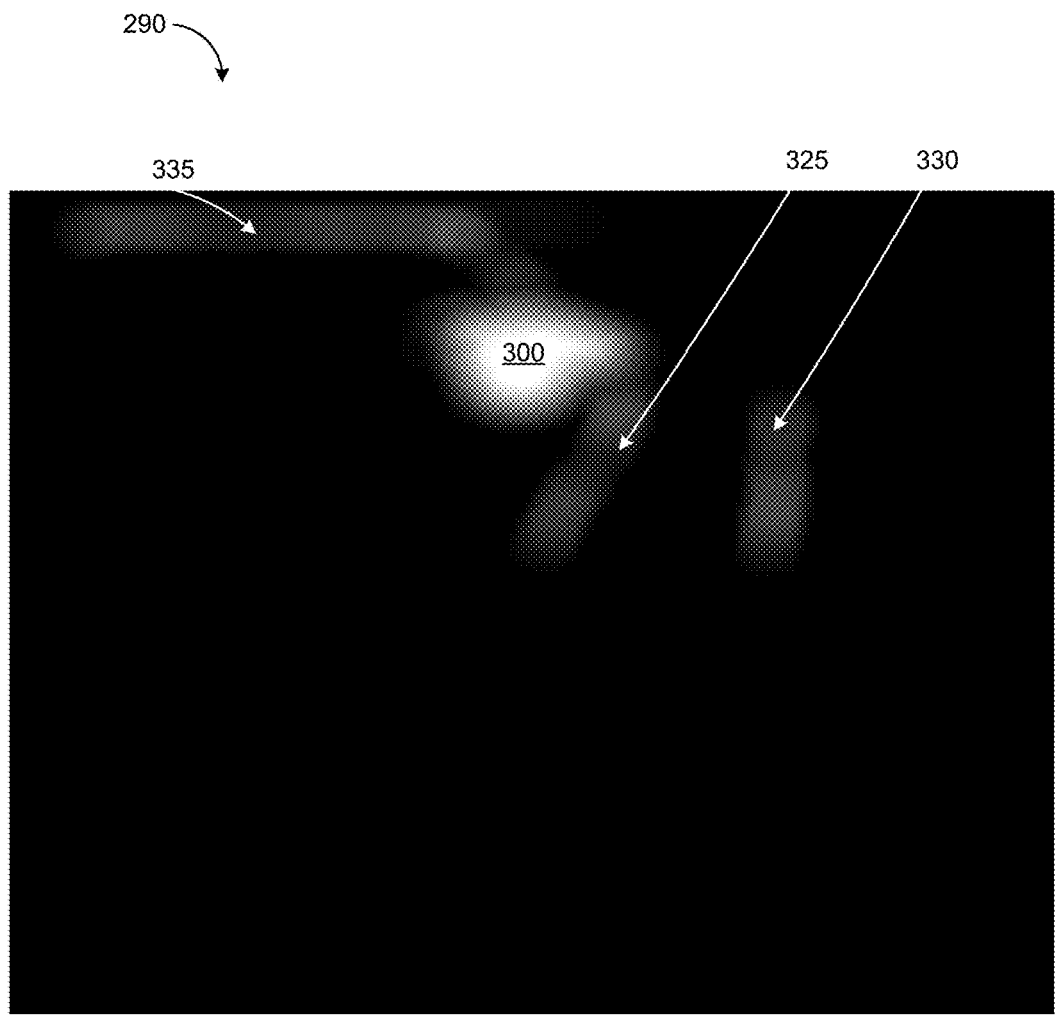
FIG. 6 is a view of an exemplary image that results from generating a bright pixel score or count or other pixel-based or intensity-based metric in a predefined neighborhood surrounding a contrast cloud in accordance with an illustrative embodiment of the disclosure.

In step A5, for each image pixel in the binary image created in step A3, the number of bright pixels inside a neighborhood area that is similar to the typical sizes of the contrast clouds that need detection is counted. Typical neighborhood areas surrounding the contrast cloud can be disk shaped, rectangular shaped, or any arbitrary shape. In one embodiment, a dimension of the neighborhood is less than about 5 mm. In one embodiment, a dimension of the neighborhood range from about 1 mm to about 4 cm. In one embodiment, the dimension is a diameter, a chord, or a line segment. FIG. 6 illustrates an exemplary image 290 that results from counting the bright white pixels 300, 325, 330, 335 in the bright white regions of the image of FIG. 5, including in a predefined neighborhood surrounding the contrast cloud 300.

In step A6, adaptive thresholding is used on each pixel from the image created in step A5. The adaptive threshold being used is one that relates to the size of the neighborhood used to create the image in step A5, as shown in FIG. 6. In step A7, a component filter is used to remove large components from the image generated in step A6. In FIG. 6 the image 290 shown results after the step of counting bright pixels in a predefined neighborhood is performed.

Figure 7:
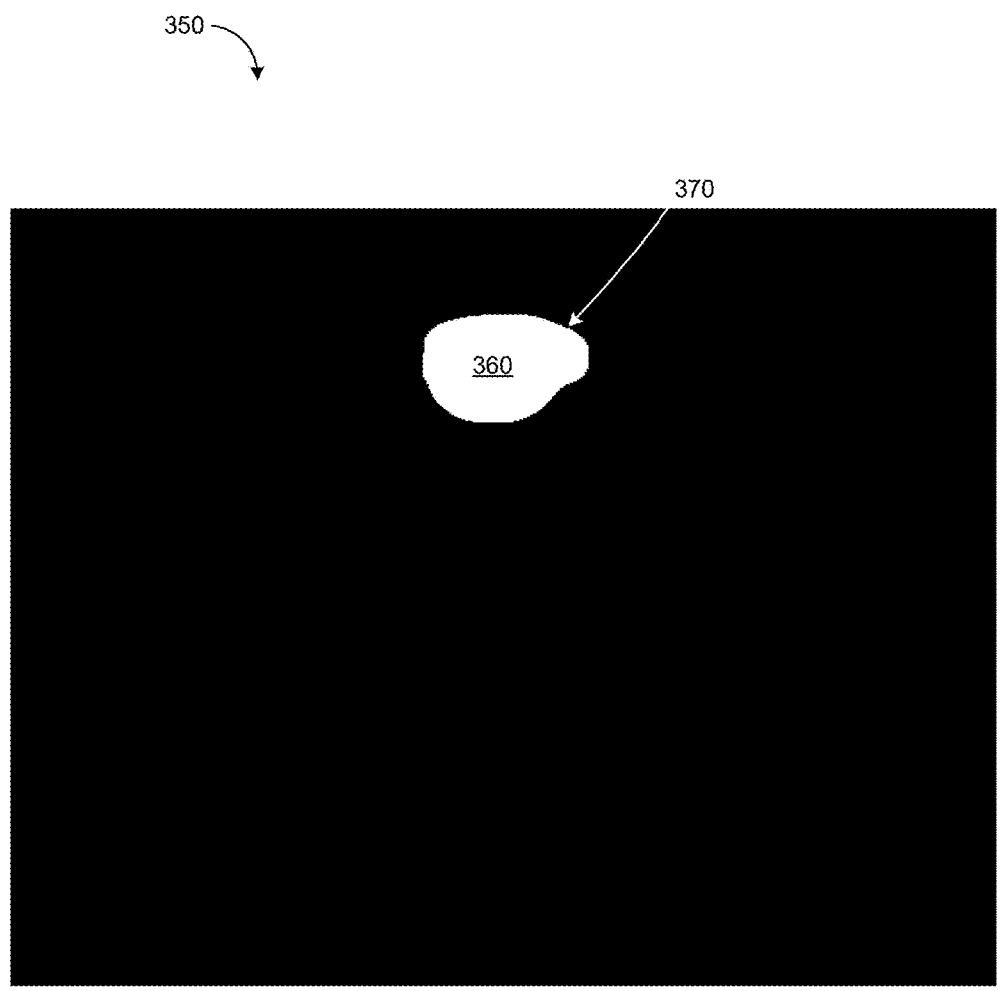
FIG. 7 is a view of an exemplary image in which a potential position and size of a contrast cloud from an image frame has been detected in accordance with an illustrative embodiment of the disclosure.

In step A8, a dilating mask step can optionally be used with a mask expanding image processing operator such as an image expanding kernel to increase the cloud mask size. FIG. 7 illustrates an exemplary image 350 in which a potential position and size of a contrast cloud from a single x-ray frame has been detected. A dilated cloud mask 360 is shown with a border or boundary 370. This is used to create a cloud mask of the contrast cloud in step A10. The cloud mask can individually and if aggregated define a region of uncertainty respect to which the presence of the contrast cloud. Expanding the mask reduces the likelihood of tracking the probe in the cloud region. The cloud region is detected and defined as an exclusion zone in one embodiment.

In steps B1-B4, optional processing steps can be used for fusing cloud masks from multiple images. In step B1, cloud masks from multiple images are used together to create a single fused mask. A pixel-wise OR operator can be used to obtain a merged contrast cloud mask incorporating information from multiple x-ray frames, in step B2. After obtaining the merged mask, another component-based filter can be used to remove small components or components that are out of the region of interest in step B3. The use of multiple x-ray frames is advantageous given the expansion and dispersal of the cloud over a time period following the contrast solutions initial delivery.

Figure 8:
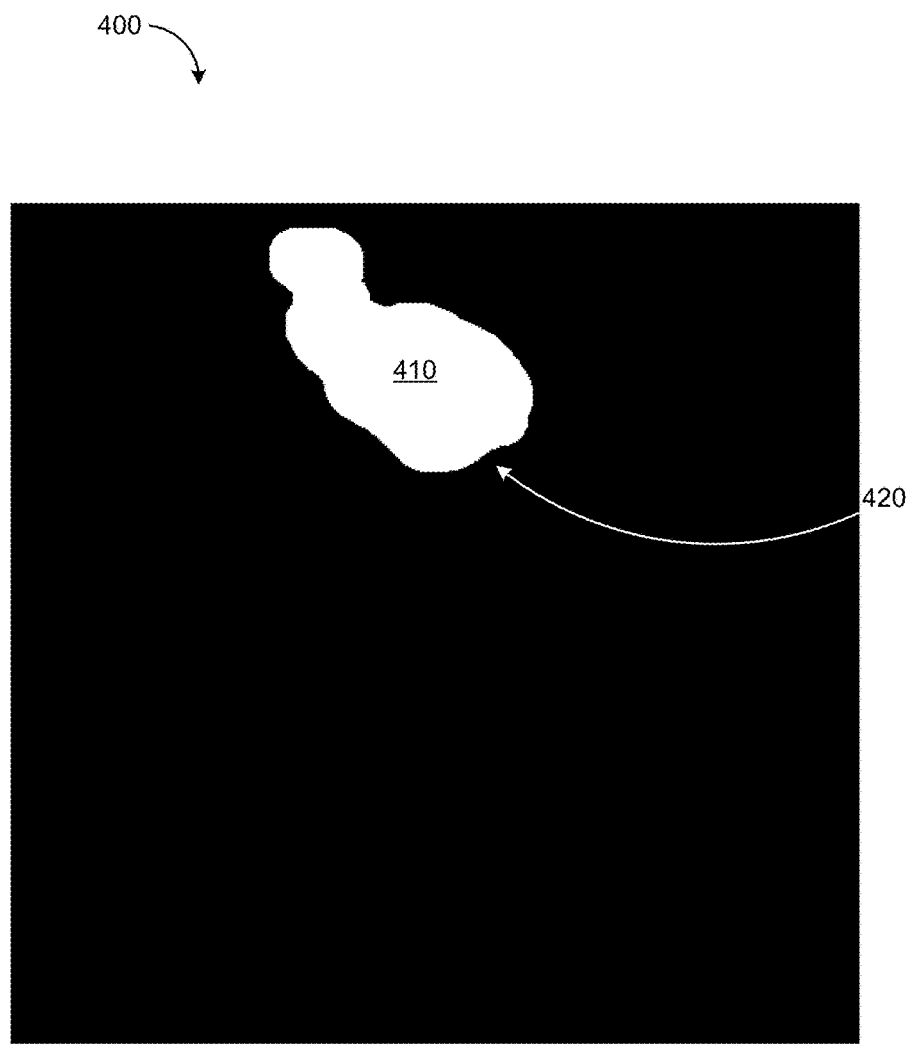
FIG. 8 is a view of an exemplary fused cloud mask from a plurality of image frames in accordance with an illustrative embodiment of the disclosure.

In step B4, the cloud masks from each frame can be fused, as illustrated in FIG. 8 which illustrates an exemplary image 160 of a fused contrast cloud mask 410 from an x-ray image sequence. This mask can be generated and applied to the image to identify the contrast cloud regions, which may include a buffer zone around them as a safety factor. These identified contrast cloud regions can then be stored in memory as ignore/avoid regions when performing additional image processing. In one embodiment, the fused cloud mask of FIG. 8 is derived by taking a pixel wise OR between multiple cloud masks.

Guidewire and Thin Element Detection Related Methods and Analysis

In another aspect, a method is provided for detecting the location of wires, such as thin metallic wires, on x-ray images, for example, x-ray angiography. Metallic wires used in the types of procedures described herein can include guidewires or wires with physiological gauges for measuring physiological conditions in the area surrounding the wire. For example, a wire with a physiological gauge or detector can be in the form of a pressure wire, or a wire that includes gauges for measuring any other conditions, including but not limited to temperature, magnetism, impedance and electrical current and/or voltage.

Guidewire extraction methods as described herein can be used to produce stable and consistent vessel centerlines in multiple frames. Once a guidewire is detected and extracted, the systems and methods described herein can use guidewire position information to define a consistent and stable position. For example, in one embodiment a detected guidewire position is selected to define one of the vessel centerline end-points in all angiography frames. In one embodiment, the detected guidewire position selected after detection is a distal detected guidewire position. Thus, having a guidewire located in the distal part of the investigated vessel can be used for reducing the registration and cross-frame errors.

Automatic extraction of a wire location and/or a wire tip location is important for various diagnostic procedures. For example, a metallic wire can include a physiological measurement gauge, and the location of the wire can be used to automatically associate a measurement from the gauge to its corresponding anatomical position. In another example, when a metallic wire is moved in the x-ray scan area an automatic trajectory extraction can be applied. In addition, when a wire is anchored at a specific anatomical location, automatic detection of consistent anatomical positions can be accomplished using this method.

Figure 9:
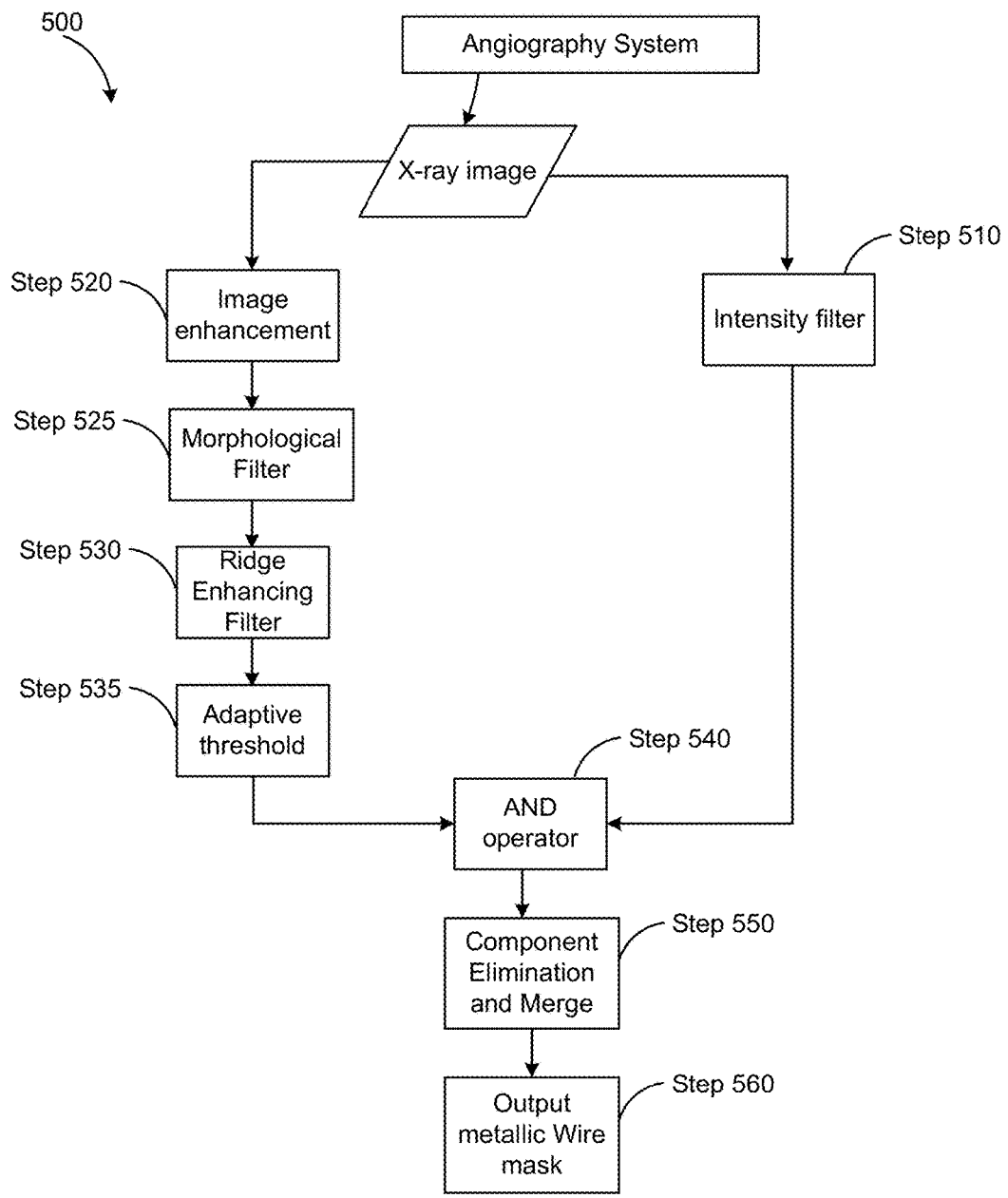
FIG. 9 is a flowchart illustrating a method of detecting a metallic wire in accordance with an illustrative embodiment of the disclosure.
Figure 10:
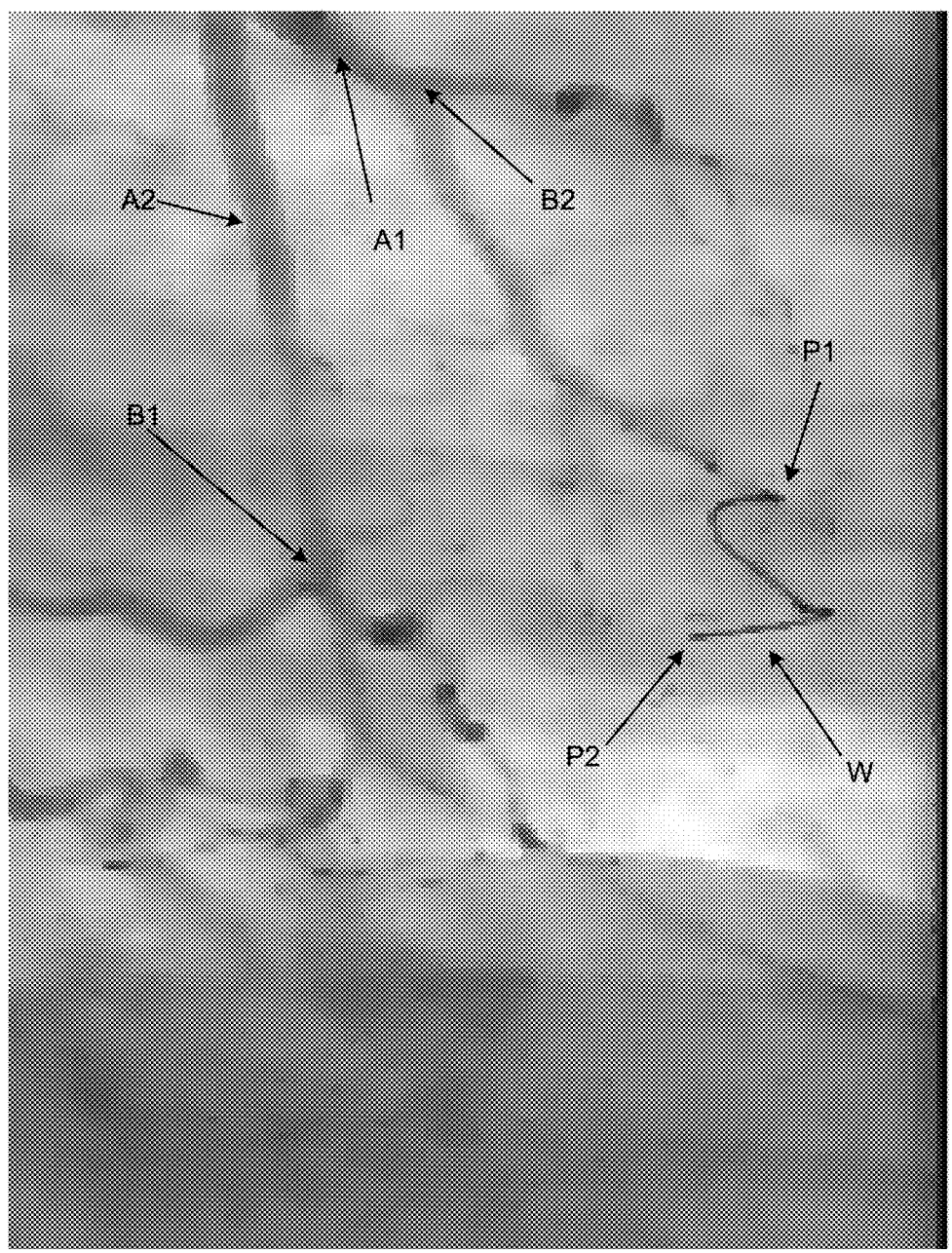
FIG. 10 is a view of an exemplary image that has been enhanced to show elongated structures such as candidate wires in accordance with an illustrative embodiment of the disclosure.

FIG. 9 illustrates a flowchart 500 of a method for detecting a wire in an x-ray image. The steps of the process flow can be performed for an x-ray image such as an angiography image or plurality of images such as an angiography sequence or cine. In step 520, image smoothing of the x-ray image, or image sequence, is performed to enhance elongated structures in the image. This filter is a modified anisotropic diffusion filter where the filter coefficients, at each iteration, are derived from the original image intensities combined with the blob and ridge detector, a Laplacian of Gaussian (LoG). In one embodiment, the structures being elongated include one or more of vessels, guidewire s, ribs or other edge containing elements in the image data. FIG. 10 illustrates an exemplary image of an x-ray image of a vessel with a wire being detected after image smoothing has occurred. In FIG. 10, the image has been enhanced by performing an image smoothing step. As part of this process, elongate structures are enhanced. The guidewire W is shown to right and has endpoints P1 and P2. Two bifurcations B1 and B2 are shown relative to arterial branches A1 and A2.

Figure 11A:
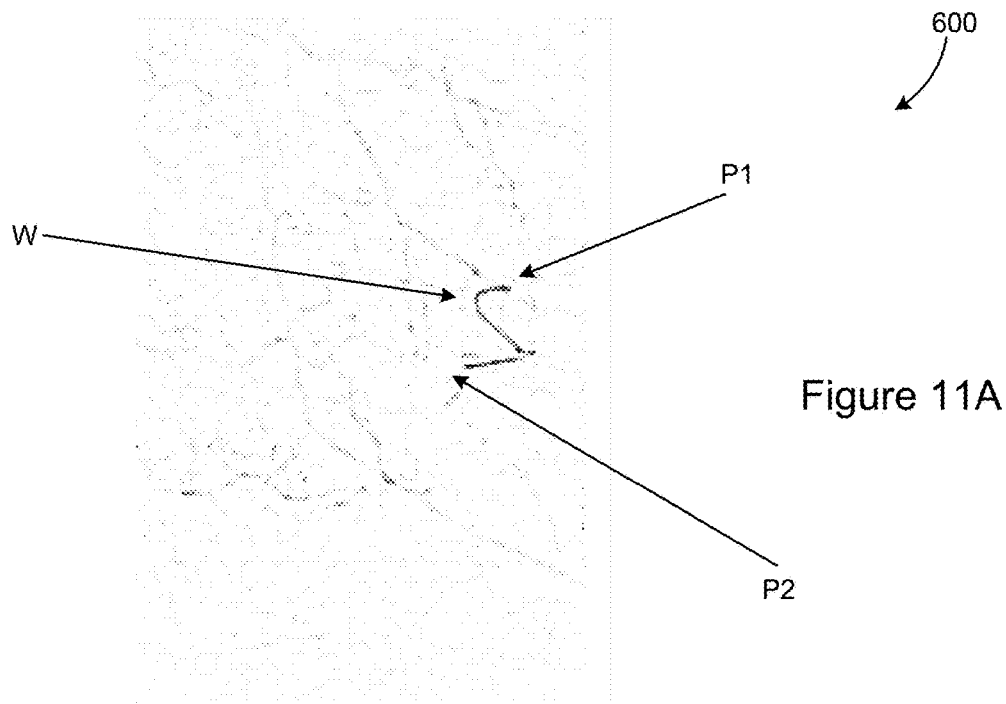
FIG. 11A is a view of an exemplary image of a wire and its two endpoints in which a bottom hat filter has been applied in accordance with an illustrative embodiment of the disclosure.

In step 525, a morphological filters applied to the image that can eliminate wide structures in the image, as shown in FIG. 11A. In one embodiment, the morphological filter is a bottom hat filter. In one embodiment, the morphological filter is any filter configured or constrained to enhance or select small scale features such as thin elements. FIG. 11A illustrates an exemplary image 600 after a morphological filter has been applied. In one embodiment, the morphological filter is a bottom hat filter. A suitable morphological filter allows for the enhancement of dark elongated elements in the image that have typical scale to the structure element used in a given morphological filter, such as for example, a bottom hat filter. In another embodiment, the morphological filter can be replaced by a median filter to produce a similar result.

Figure 11B:
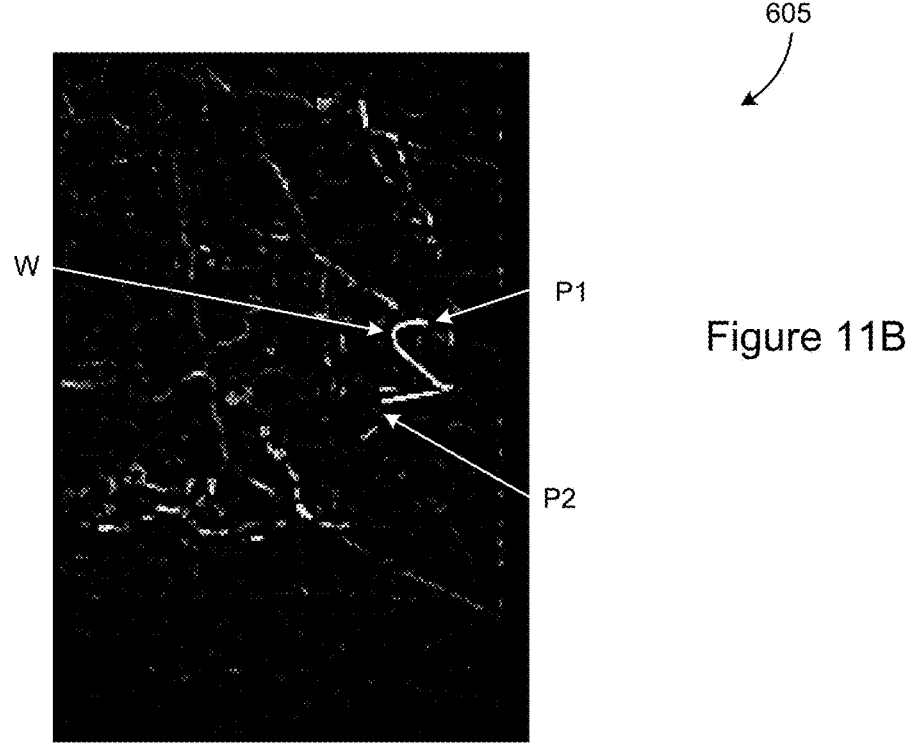
FIG. 11B is a view of an exemplary image in which an image processing filter such as a ridge filter has been applied in accordance with an illustrative embodiment of the disclosure.

In step 530, a ridge enhancing filter or detector or a vessel segmentation filter is applied as shown in FIG. 11B. In one embodiment, such a filter or detector is implemented using a ridge enhancing filter, such as a Frangi filer or other suitable filter, that is applied to the image to enhance ridges in the image, as shown in FIG. 11B. A ridge enhancing filter can include a Hessian filter, a Frangi filter, or other ridge or edge detectors.

FIG. 11B illustrates an exemplary image 605 after the ridge enhancing filter has been applied to enhance the ridge structures in the image. In this way, a ridge enhancing filter is used for the extraction of thin elongated features in the image. The ridge enhancing filter output is thresholded to produce a binary image containing thin and elongated dark elements that appear as bright pixels in the thresholded image.

Figure 12:
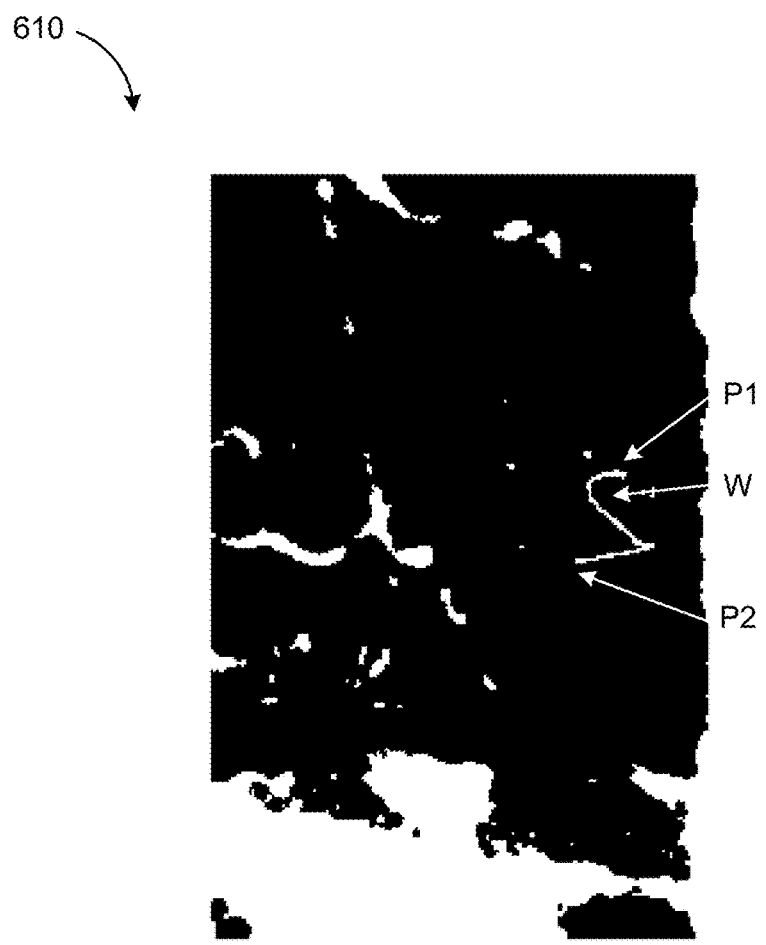
FIG. 12 is a view of an exemplary intensity threshold image of a portion of the vascular system with a wire disposed in a blood vessel in accordance with an illustrative embodiment of the disclosure.

In step 535, bright areas in the image are rejected by performing adaptive thresholding on the input image as a processing step. Metallic wires are radio-opaque, and will appear as dark elongate regions on an x-ray image. An adaptive binary threshold is applied in order to reject image areas with intensity values that are not of interest. Thus, bright areas that have an intensity greater than a threshold associated with an intensity value or range of values corresponding to dark values can be rejected in one embodiment. FIG. 12 illustrates an exemplary image 610 in which the bright areas of the image have been rejected as a result of the process of performing an intensity threshold image processing step.

In step 540, the ridge enhancing filter output result and the adaptive intensity filter result are merged using a pixel-wise AND operator, to obtain a merged metallic wire mask component. In one embodiment, the angiography image processing software modules and methods described herein connect and filter wire fragments that are detected in the images. In step 550, the wire can be extracted in fragments, and other components in the image which are not related to the wire can be detected. The wire fragments can be joined using a combined measurement of a takeoff angle and a distance between the fragments.

Figure 13:
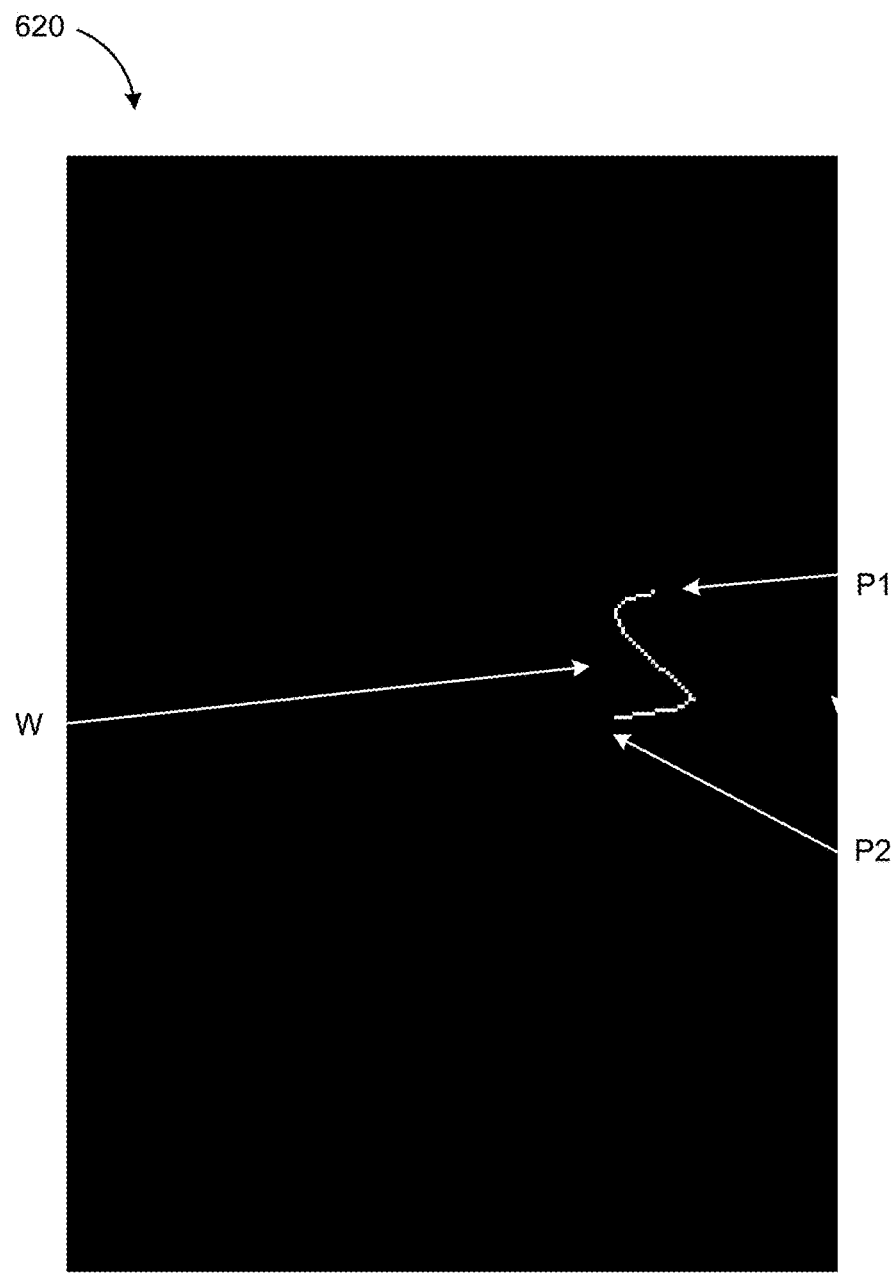
FIG. 13 is a view of an exemplary mask suitable for use during an image processing method to detect a wire such as an intravascular guidewire in an x-ray image in accordance with an illustrative embodiment of the disclosure.

In an optional step, post filtering of components and/or thinning of components can be performed to remove elements from the surrounding area that may have joined during the wire detection. The result of the image processing the preceding steps is used to create a mask of the detected wire in step 560. FIG. 13 illustrates an exemplary image of the wire mask 620 created in step 560. The mask 620 is shown with the binary levels, one intensity level is associated with the wire W and the rest of the mask is a dark or black second intensity level corresponding to the background of the image. The wire W has endpoints P1, P2, respectively, as shown. The mask 620 is displayed after performing a thinning process 560. In one embodiment, one or more of endpoints P1 and P2 can be used to set an endpoint of a vessel centerline. In one embodiment, guidewire detection is performed to identify one or more distal guidewire endpoints. The one or more distal guidewire endpoints can be selected to define a vessel centerline endpoint.

In one embodiment, the wire masking step is performed prior to tracking the vessel centerline distal end-point in one embodiment. The application of the wire mask assists in tracking the distal end-points of the vessel centerline for one or more angiography frames with increased accuracy. The identification of contrast cloud regions and avoiding such regions during marker tracking and other image processing steps facilitates having a stable and consistent centerline end-point. In turn, having a stable and consistent end-point increases cross-frame registration accuracy.

Vascular Tree Registration

Various medical applications require accurate mapping between the same anatomical locations captured at different frame during movement and deformation. For example, angiography imaging of an artery during an intravascular imaging pullback followed by stent deployment is one such application. The heart is a fast-moving organ with complex deformations. As a result, such a mapping can be difficult to create. This follows because angiography gives a 2D view of a tortuous 3D system in which vascular tree components, bifurcations, and guidewires, implants, stents and other intravascular imaging devices are overlaid on top of each to create ambiguities and overlapping regions in the angiography image which are not really present in the subject's vasculature. Various embodiments of the invention provide methods and systems to perform such a mapping using anatomical landmarks such as for example bends, anchor points and bifurcations as disclosed herein.

In addition, the disclosure also relates to methods of detecting a bifurcation extraction on angiography image. Methods for grouping bifurcations from multiple x-ray frames are also disclosed. Further, methods of detecting and grouping vessel bends positions from multiple x-ray frames are disclosed. Motion estimation for 3D vascular structures can also be performed using the detection methods described herein and tracking of landmarks and their relative movement over time and between frames. Methods to improve the accuracy of cross frame registration can be achieved by incorporating detection of anchor points based on bifurcations and bends across different x-ray frames. The other detection and exclusion processes described herein can also help improve such cross-frame registration.

In part, the disclosure relates to methods to register a vascular tree, vascular tree segments or other vascular components that are imaged on a plurality of x-ray frames such as frames of angiography data. In one embodiment, the methods can use an anchor extraction, bend points or a bifurcation point extraction as a step or stage in a given registration between a first frame and a second frame, for example. In one embodiment, the methods can use a vessel extraction as a step or stage in a given registration between a first frame and a second frame, for example.

As described herein, an angiography image can include one or more bifurcations. The disclosure describes image data processing and analysis steps to extract or otherwise identify the bifurcation on a per frame and cross frame basis. In one embodiment, methods are described for grouping bifurcations from multiple x-ray frames. The disclosure describes image data processing and analysis steps to extract or otherwise identify the vessel bends on a per frame and on a cross frame basis. In one embodiment, methods are described for grouping vessel bends and bifurcation from multiple x-ray frames.

A method for registering vascular trees extracted from different contrast enhanced x-ray frames, for example during x-ray angiography is described herein. In one embodiment, the vessel centerlines are known or treated as known for each of the vascular branches of interest. The process of detecting such centerlines can be performed using various methods as described in U.S. Pat. No. 9,351,698, the disclosure of which is incorporated by reference herein in its entirety. In one embodiment, a registration method described herein uses bifurcation points (if they exist) and the bending points (if they exist) as "anchors" for matching anatomical positions between different frames. Once the set of matching "anchor points" is obtained, the registration is based on interpolating for matching positions based on relative geodesic distance as measured along the arc-length of the centerlines. Various distance metrics can be used as appropriate.

Furthermore, the "anchors points" fusion can be used to generate an estimation of the three-dimensional cardiac motion and deformation. Using a pair of angiographic images (2D projections), from the same cardiac phase, one can obtain three-dimensional reconstruction of the tree vessels. These 3-D vessels structures reconstructions at multiple phases of the cardiac cycle are of interest for 3D heart motion understanding. The displacements of these anchor points on each view along the image sequences induce a way of computing the motion estimation in the 3D vascular structure. Additional details relating to methods of performing "anchor points" matching for interframe registration of vascular trees are described below and otherwise herein.

Figure 14:
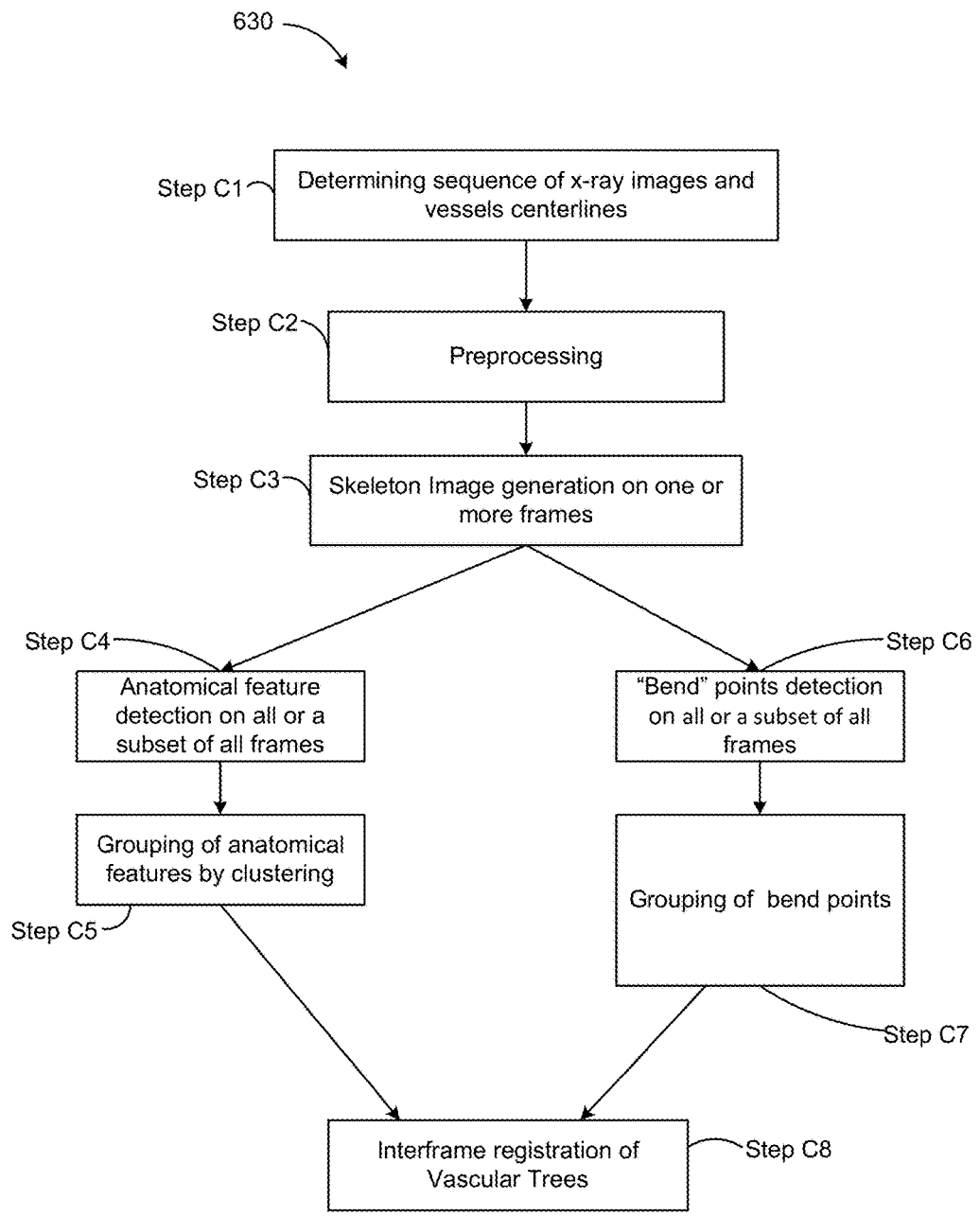
FIG. 14 is a flowchart illustrating a method of registering vascular tree segments in multiple frames by one or more detected bends and bifurcations of a vascular structure in accordance with an illustrative embodiment of the disclosure.

Anatomical Feature Detection—Bifurcation Points Extraction/Detection and Grouping FIG. 14 shows an exemplary process flow 630 suitable for registering points associated with a cardiac system such as vascular trees between a first and a second angiography frame. This process flow can be used to detect anatomical features and use them for cross-frame/interframe registration. Cross-frame registration can be also accomplished by other anatomical features or anatomical landmarks found along the vessel. The method 630 can be used to perform interframe registration of vascular trees as shown.

In one embodiment, the process of detecting anatomical features such as bifurcation points such as the split of an artery into a first and a second blood vessel or bends for a given vascular tree and the associated process of grouping such points can be implemented using various data transformation and image processing steps. Initially, the method determines a sequence of x-ray images and associated centerlines Step C1 for processing such as by user selection or other criteria.

Figure 15A:
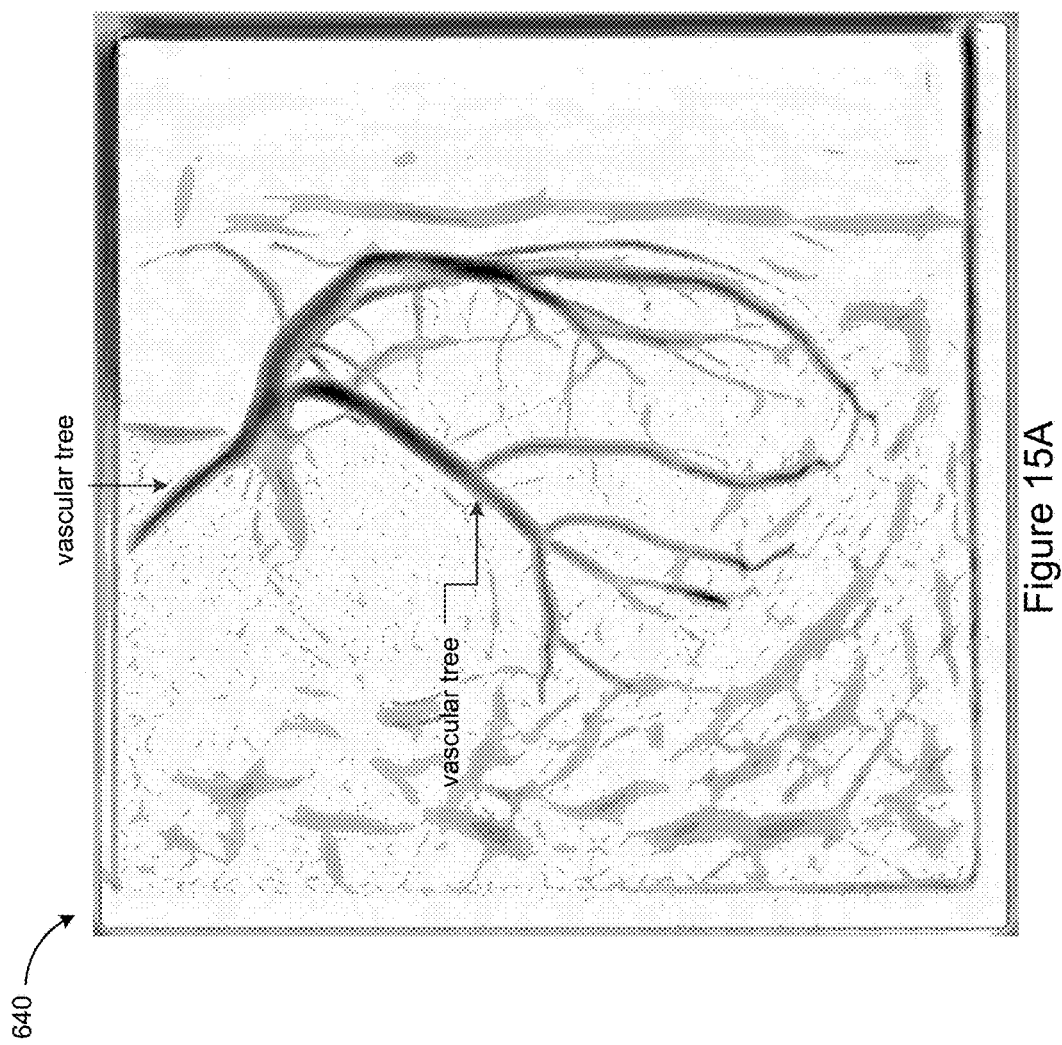
FIG. 15A is an angiography frame that has been preprocessed prior to skeleton image generation in accordance with an illustrative embodiment of the disclosure.

Centerlines can be determined as described herein. Theses x-ray images undergo preprocessing Step C2. An example of such a preprocessed image 640 is shown in FIG. 15A. In one embodiment, a skeleton image is generated around each centerline of interest as the preprocessing step. Various arterial branches and the associated bends and take off junctions and angles thereof are evident and detectable as a result of the lightening of peripheral features and the darkening of arterial features as shown in FIG. 15A.

FIG. 15B and 15C are an original angiography image and a skeleton of one the vessels in that image and a portion of its periphery environment, respectfully, after the application of image processing and data analysis in accordance with an illustrative embodiment of the disclosure. The skeleton image of FIG. 15C corresponds to the output of Step C3. Still referring to FIG. 14, the method includes steps that can be grouped into two processing paths or categories. In one embodiment, the two processing paths or categories can relate to a first anatomical feature or anatomical landmark and one relating to bifurcations and one relating to bend points.

In one embodiment, the bifurcation related portion of the method includes the steps of detecting bifurcations on all or a subset of all frames Step C4 and grouping of bifurcations by clustering Step C5. The bend related portion of the method includes the steps of detecting "bend" points detection on all or a subset of all frames Step C6 and grouping of the detected bend points Step C7. These groupings of bifurcations and bend points are in turn used to perform interframe registration of the vascular trees Step C8 or other vascular structures or subsets thereof. In general, any groups of a first anatomical features and a second anatomical feature can be grouped or clustered as described herein and in turn used to perform interframe registration of the vascular trees Step C8 or other vascular structures or subsets thereof.

Bifurcation Detection—Feature Extraction Related Features

In one embodiment, performing feature extraction relative to a bifurcation such as described with regard to Step C4 of FIG. 14 includes various steps. In one embodiment, detecting the bifurcation such as by performing feature extraction includes applying a shadow removal filter on the original image. In one embodiment, this filtering is performed using the morphological operation of bottom hat with a large structure element, which reduces the effect of heart shadows, of diaphragm and further enhances vessels. The output from the prior step can be processed using a Hessian based filter image.

In one embodiment, the output from the Hessian filtering is adaptively thresholded to generate a binary image. In one embodiment, a skeleton generating algorithm is applied to the binary image in to obtain a skeleton image. In turn, the skeleton image can be improved by eliminating small components from the skeleton image. In one embodiment, the small components are less than about 5 pixels. In one embodiment, the small components are less than about 10 pixels. In one embodiment, the small components are less than about 15 pixels. In one embodiment, the small components are less than about 20 pixels. In one embodiment, the small components are less than about 25 pixels. In one embodiment, the small components are less than about 30 pixels.

In one embodiment, after the generation of a skeleton image and any subsequent enhancement, the method can include the step of detecting a set of bifurcations on each frame such as for example on each frame's centerline. In one embodiment, the bifurcations are identified as junctions in the skeleton. In order to obtain accurate results of bifurcation points, elimination of false bifurcation-like features such as vessel crossings and ribs is needed. For that purposes a series of one or more filters is applied as follows.

In one embodiment, a rib filter is applied to reduce any contribution that the rib cage or individual ribs may show up in the image and be misconstrued as part of the vascular tree structure. Ribs are nearly static with respect to vessels that move faster. Any filter that is configured to reduce static elements from the image can be used here to image a rib or other static element. In one embodiment, a temporal filter is used such the filter operates to take every pixel in the entire image sequence and filter it as if it was a 1D signal. In addition, it is also desirable, in some embodiments, to filter the collection of these signals by a high pass filter, thus eliminating static background. An average image is calculated from multiple frames and then deducted from the frame of interest. In this way, a static element such as a rib can be removed from or ignored when performing analysis and image processing on a frame of x-ray image data.

In one embodiment, a vessel crossing filter or detector is applied to an x-ray image frame. In a given frame, vessel crossings may appear as two adjacent bifurcations taking off at opposite directions. The take-off angle of the branch with respect to the main centerline is used to resolve the occurrence of such vessel crossings and the associated potential for co-registration errors due to the crossing of vessels. In addition, vessel crossings are also addressed by excluding bifurcations situated on different sides of the main centerline and satisfy the condition of having adjacent take off location along the main centerline and absolute angle difference close to 180°.

The association or grouping process of an anatomic features such as the bifurcations is based on clustering. This clustering or grouping process corresponds to Step C5 from FIG. 14. In this context, a cluster refers to a single bifurcation extracted from multiple frames. If the same bifurcation is detected on multiple frames, even if in slightly different positions and orientations, the set of a representative bifurcation across frames should form a cluster indicative of it being the same bifurcation imaged at different times on different frames. In one embodiment, one or more links or vectors can be identified and measured between clusters. The distance metric between two clusters takes into consideration differences between the bifurcations' features or whatever feature is being evaluated and compared. These features can include: angles with respect to the main vessel centerlines, the normalized arc length of the bifurcation and average image intensity along the bifurcations branches, bifurcation scale(or width), absolute angle on the angiography image, and bifurcation lumen shape. Thus, the foregoing features can be used to identify differences and generate a distance metric to evaluate and compare the clustering behavior of a given feature.

In one embodiment, a bifurcation descriptor space or model is generated using various features. The features include one or more of a mean image intensity value on the branch (I values), a branch take-off absolute angle (A values), and a normalized arc length of the branch (S values). A similarity measure and or a distance measure/metric can be used to associate data points in feature space. An example of such metric can be the Euclidean metric $D(C_i, C_j)$ defined below.

$$D(C_i, C_j) = \operatorname{sqrt}((I_i - I_j)^2 + (A_i - A_j)^2 + (S_i - S_j)^2)$$

For $D(C_i, C_j)$, I refers to a mean image intensity, A refers to an absolute angle of the take-off branch and S refers to normalized arc length of the branch. The indices i and j correspond to different angiography frames i and j.

Clusters of bifurcation datasets representing the same bifurcation in multiple frames are detected and/or selected. The process of detecting/selecting can be performed using feature extraction. The use of feature extraction is beneficial given the presence of image noise in the clusters and missing information. In one embodiment, a bifurcation is detected on multiple image frames such that this set of detections across frames can be clustered together to help validate that bifurcation as being the same one across different frames. Feature extraction includes the step of filter excess data such as image noise in one embodiment. In addition, feature extraction can include the step of completing missing information in one or more clusters such as by interpolation or other processes.

Clusters of certain size (large clusters versus small or medium sized clusters) are selected for the next processing step in one embodiment. A cluster is identified as of a suitably large size for selection and further processing based on the number of its representatives compared to the set of angiography frames captured during the OCT pullback. Once selected, the clusters are used in a cluster consolidating step. The process of consolidating the clusters generates a set of clusters each having a single representative from each frame of interest.

Figure 16B:
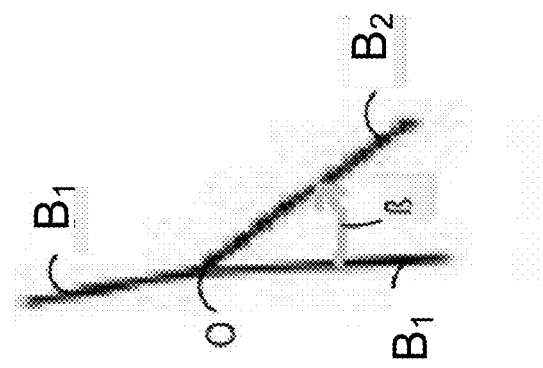
FIG. 16A is a subset of an angiography image corresponding to a portion of the vascular system and FIG. 16B is a representation of that portion of the vascular system showing a bifurcation as part of a vascular tree and an associated angle β between a vessel branch and its originating (parent) vessel in accordance with an illustrative embodiment of the disclosure.
Figure 16A:
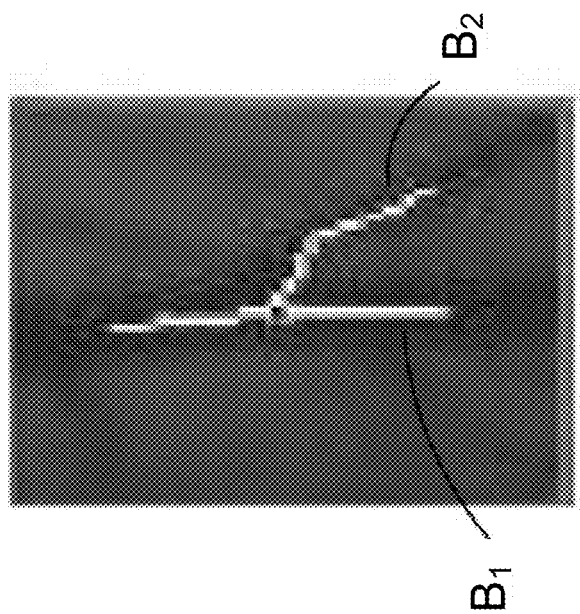

FIG. 16A shows a subset of an angiography image with a bifurcation formed from two branches B1 and B2. FIG. 16B is a representation of that portion of the vascular system showing a bifurcation as part of a vascular tree and an associated angle β between a vessel branch and its originating (parent) vessel in accordance with an illustrative embodiment of the disclosure. As show, in FIG. 16B, the angle of bifurcation with respect to (parent) vessel branch B1 is shown in the schematic representation of the bifurcation as angle β. The angle β is formed from the junction of branch B1 and branch B2 and is shown as opening from B1 to B2 by the arrow. Theses bifurcations are plotted or otherwise grouped based on the angle and arc length in one embodiment as shown in FIG. 17A.

Cluster Consolidation

Figure 17A:
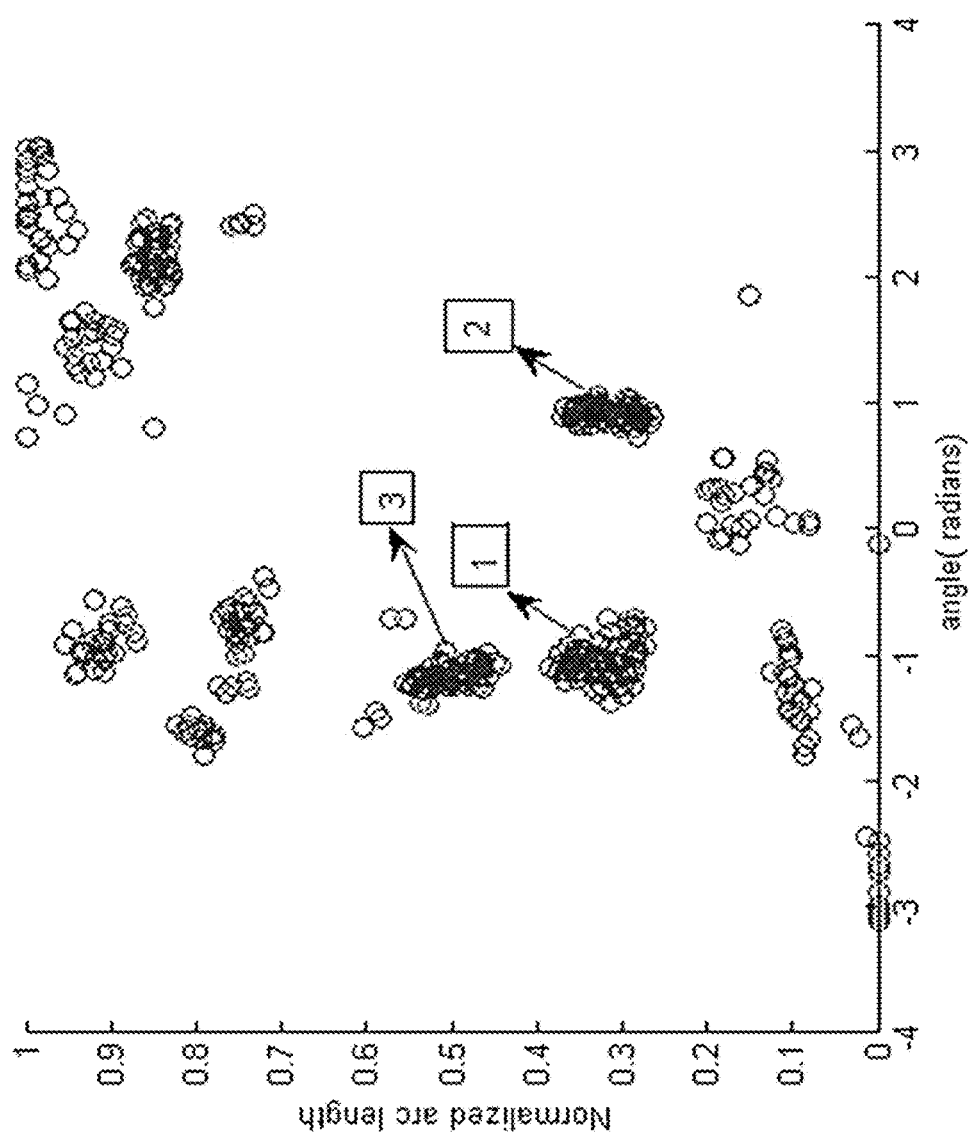
FIG. 17A is a plot that shows a plurality of clusters as generated from plotting a normalized arc length (vertical axis) of a branch segment versus angle measurements (horizontal axis) in accordance with an illustrative embodiment of the disclosure.

FIG. 17A shows a plurality of clusters as generated from plotting a normalized arc length (vertical axis) versus angle measurements (horizontal axis). Three clusters of interest are labeled 1, 2 and 3. Cluster 1 is to the left of cluster 2 and includes a greater number of data points. The data points are show as circular regions. Cluster 3 is above cluster 1 and has a greater number of overlapping data points along a rectangular region span the cluster from its top to bottom. In one embodiment, a redundancy elimination step is performed.

Figure 17B:
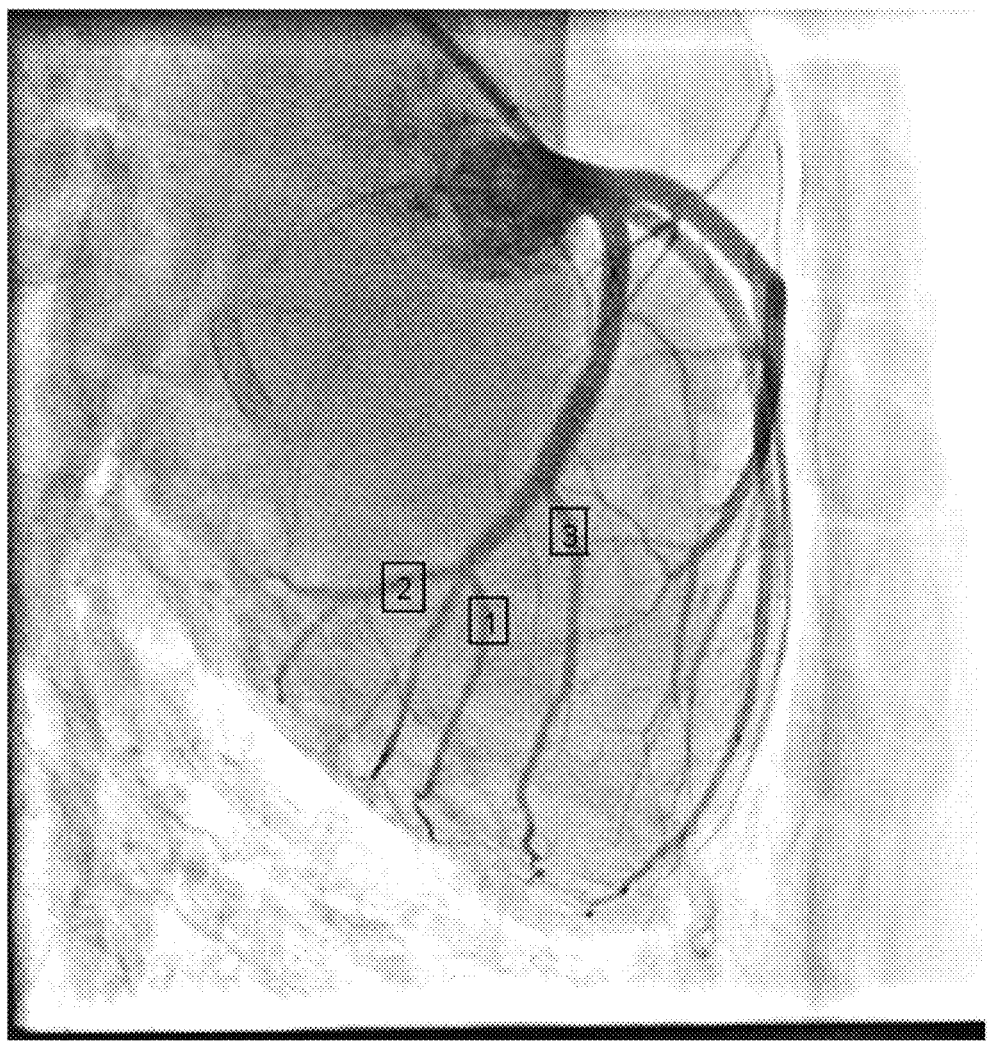
FIG. 17B shows an angiography image frame depicting various branches (2, 1, and 3) that are associated with a particular cluster in the plot of FIG. 17A in accordance with an illustrative embodiment of the disclosure.

For example, if clusters that contain multiple representatives from the same frame, a single point that is closest to the cluster centroid is selected. FIG. 17B shows the corresponding locus for each cluster on the frame of angiography data that was analyzed to generate the clusters. It is desirable to have a single cluster representative from each frame. Therefore, if a cluster lacks a representative from a frame/s, then as a substitute for the missing information interpolated values based on nearest frames will be used to complete the cluster. Any type of interpolation (Linear, Cyclic, spline-based, curve fit, etc.) can be implemented to complete a cluster or define a boundary for such a cluster. The elements of the cluster are the bases for treating such an element as the same element across images in one embodiment.

Cluster Selection

Each bifurcation cluster is assigned a quality grade that is used for cluster selection. The following factors enter the grade: arc-length standard deviation, normalized arc-length standard deviation, angle difference standard deviation, proximity to other bifurcation clusters (based on distances between centroids of different clusters), average number of redundant bifurcation records per frames, average number of missing bifurcation records per frame. A weighted average including these various factors can be used to generate the grade. The clusters with best grades are finally chosen.

Vessel Bend Feature Extraction/Detection and Features

As noted in FIG. 14, the method also includes a bend related path including steps C6 and C7. Additional details relating to these steps follow. A set of anatomical "anchors" are extracted as features based on positions of vessel bends. Vessel bends are defined as points where the vessel changes it direction to create a corner-like structures that exhibits high curvature. At each frame a multi scale curvature or curvature-analog is extracted from the vessel centerlines described earlier.

In one embodiment, the method uses a tracking or shortest path algorithm such as the Viterbi algorithm to determine the positions of each bend in all frames or in a sampling of frames. In various embodiments, feature extraction is used to detect anatomical and other features or landmarks in a given image frame. In one embodiment, the feature of a shortest path is extracted from all frames of interest by optimizing a cost criterion that is based on the bend angle size, the bend location along the vessel centerline in terms of arc-length or normalized arc-length, and the angle deviation difference between two bends in consecutive frames. The set of bends and bifurcations that span the various frames are used to identify a path or otherwise perform registration between angiography frames in one embodiment.

After the cost criterion is calculated from multiple starting points, solutions are extracted based on the ranking of the associated cost criterion for a given solution. After all bend candidates from multiple frames are extracted, a filtering step may be applied to eliminate solution originating from small bends or bends that that display inconsistent positions along the vessel centerline.

Figures 18A, 18B:
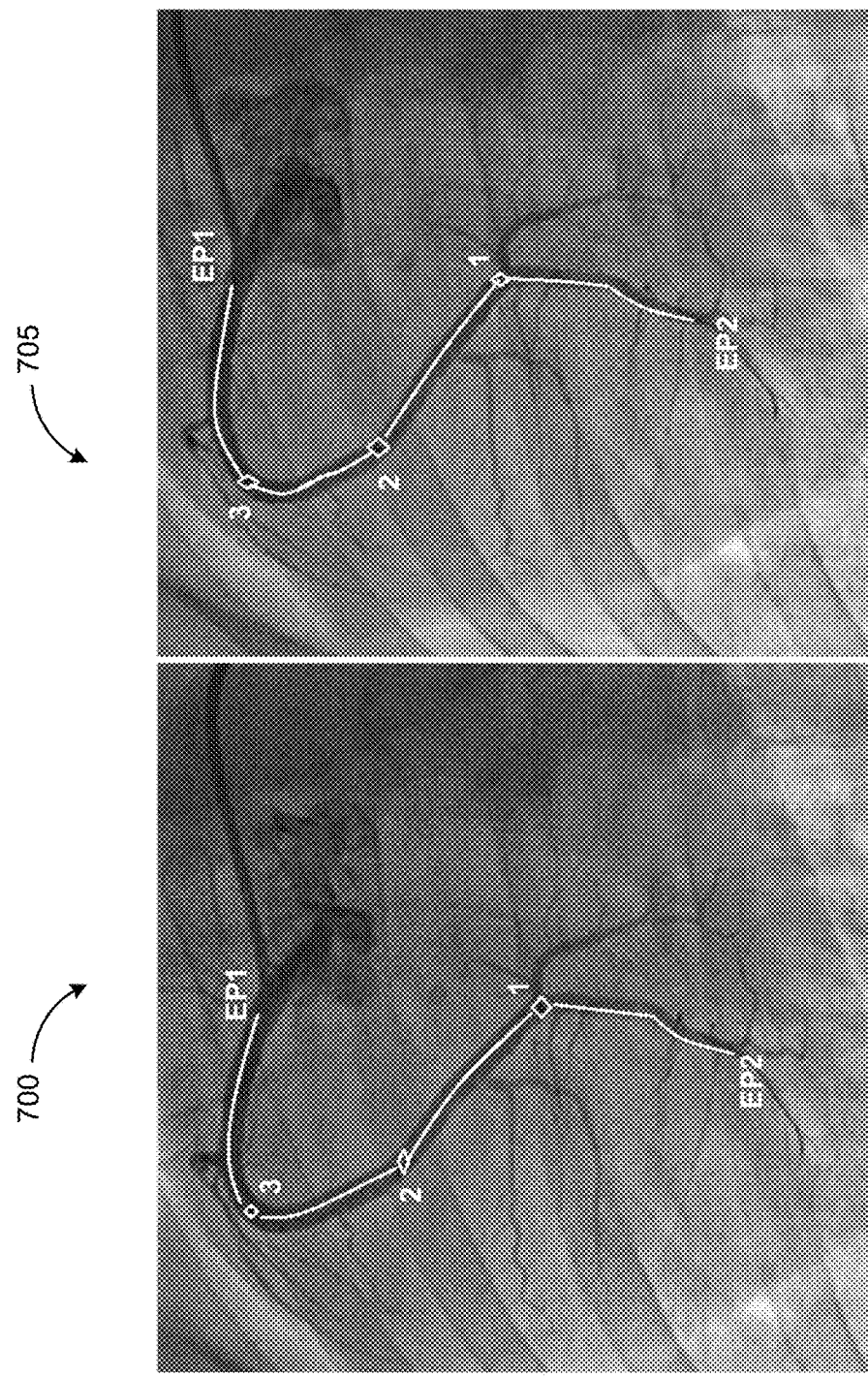
FIGS. 18A and 18B are frames of angiography data that show a path traced through various blood vessel segments overlaid thereon along with labels identifying junctions or bends identified using the methods and systems described herein in accordance with an illustrative embodiment of the disclosure.

FIG. 18A and 18B depict two angiography frames of multiple vascular trees. In each frame 700, 705, the three bends were detected from the two x-ray frames. Centerline detection was performed on each x-ray frame. The resulting detected centerlines are depicted by a white line overlaid on each frame. Bending detection was also performed with respect to each x-ray frame. The bend positions are shown by white diamonds. Three bends are shown in each of the left image frame 700 and right image frame 705 numbered 1, 2, and 3 from the bottom to the top. Each vessel centerline traces a path through the artery along bends 3, 2, and 1. A position of a particular bend in all angiography frames can be used as an anatomical anchor or reference point to accurately identify cross frame positions.

Additional Supporting Details Relating to Skeletons and Vessel Centerline/Generation Further, in one embodiment, as part of the preprocessing of the angiography images, anatomic feature detection is performed. In one embodiment, this can be performed to generate certain a priori information relating to the path the imaging probe takes through the blood vessel. The generation of line segments such as through a skeleton generation process can be used for feature detection. In one embodiment, a skeleton is a static object such as one or more line segments created to help trace the blood vessels of a subject being imaged.

The use of a skeleton or line segment based approach to generate a candidate path through the blood vessel for the data collection probe which can be used to inform centerline generation and marker tracking offers several advantages to forgoing the use of such an approach. For example, the skeleton based approach can prevent or eliminate certain vessel centerlines being generated that would otherwise pass through a side branch or the imaging probe catheter.

Generating skeletons provides a method to determine an initial candidate for the geometry of the blood vessel being imaged and side branches and other blood vessels as a map or framework to facilitate centerline generation. By generating skeletons, it is possible to extract points of interest such as bifurcation points and vessel segments, to stabilize tracking of markers and vessel centerlines and to verify tracking quality across frames of angiography image data.

In one embodiment, the process of generating skeletons to detect anatomic features like side branches and vessel geometry is implemented during preprocessing of the angiography images. Skeletons can be used for detecting anatomical features such as main bifurcation and extrapolation point. In addition, skeletons can be used for detecting and generating a smooth vessel centerline. For example, skeletons can be used with a shortest path algorithm, such a Viterbi, Dijkstra algorithm or other algorithms to facilitate centerline creation. The skeletons can be generated based on preprocessed Hessian images. A user selected point on an angiography image relating to a guidewire position can be used to reduce noise and facilitate skeleton generation. In other embodiments, this can be implemented by selecting a point based on image features.

In one embodiment, one or more software modules are used to generate and track a vessel centerline for a given frame of angiography data. In one embodiment, a vessel centerline also referred to herein as a centerline is a model or simulation that is generated based on an iteratively evaluation of each candidate subset of a frame of angiographic data for marker bands associated with the optical or acoustic sensor or other imaging or data collecting sensor introduced during the angiographic data collection.

In one embodiment, a dynamic program software module such as a software module implementing one or more steps of any suitable shortest or optical path determining algorithm, such as, for example, the Viterbi algorithm can be used to track the marker bands. In one embodiment, the Viterbi algorithm is used for radiopaque marker tracking. The creation and tracking of the centerlines are typically handled by other algorithms or combinations thereof. Centerline tracking can be enhanced by using feature detection such as guidewire or landmark detection to define an endpoint of a centerline. By defining a centerline endpoint, cross-frame registration and confidence in centerline determination is advantageously increased.

The use of arrow heads showing directionality in a given figure or the lack thereof are not intended to limit or require a direction in which information can flow. For a given connector, such as the arrows and lines shown connecting the elements shown in FIG. 1, for example, information can flow in one or more directions or in only one direction as suitable for a given embodiment. The connections can include various suitable data transmitting connections such as optical, wire, power, wireless, or electrical connections. Non-limiting Software Features and Embodiments for Implementing Angiography and Intravascular Data Collection Methods and Systems The following description is intended to provide an overview of device hardware and other operating components suitable for performing the methods of the disclosure described herein. This description is not intended to limit the applicable environments or the scope of the disclosure. Similarly, the hardware and other operating components may be suitable as part of the apparatuses described above. The disclosure can be practiced with other system configurations, including personal computers, multiprocessor systems, microprocessor-based or programmable electronic devices, network PCs, minicomputers, mainframe computers, and the like.

Some portions of the detailed description are presented in terms of algorithms and symbolic representations of operations on data bits within a computer memory. These algorithmic descriptions and representations can be used by those skilled in the computer and software related fields. In one embodiment, an algorithm is here, and generally, conceived to be a self-consistent sequence of operations leading to a desired result. The operations performed as methods stops or otherwise described herein are those requiring physical manipulations of physical quantities. Usually, though not necessarily, these quantities take the form of electrical or magnetic signals capable of being stored, transferred, combined, transformed, compared, and otherwise manipulated.

Unless specifically stated otherwise as apparent from the following discussion, it is appreciated that throughout the description, discussions utilizing terms such as "processing" or "computing" or "calculating" or "comparing" or "arc length measuring" or "detecting" or "tracing" or "masking" or "sampling" "clustering" "feature extracting" or "adaptively thresholding" or "operating" or "generating" or "determining" or "displaying" or "finding" or "extracting" or "filtering" or "avoiding" or "excluding" or "interpolating" or "optimizing" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present disclosure, in some embodiments, also relates to the apparatus for performing the operations herein. This apparatus may be specially constructed for the required purposes, or it may comprise a general-purpose computer selectively activated or reconfigured by a computer program stored in the computer.

The algorithms and displays presented herein are not inherently related to any particular computer or other apparatus. Various general purpose systems may be used with programs in accordance with the teachings herein, or it may prove convenient to construct more specialized apparatus to perform the required method steps. The required structure for a variety of these systems will appear from the description below.

Embodiments of the disclosure may be implemented in many different forms, including, but in no way limited to, computer program logic for use with a processor (e.g., a microprocessor, microcontroller, digital signal processor, or general purpose computer), programmable logic for use with a programmable logic device, (e.g., a Field Programmable Gate Array (FPGA) or other PLD), discrete components, integrated circuitry (e.g., an Application Specific Integrated Circuit (ASIC)), or any other means including any combination thereof. In a typical embodiment of the present disclosure, some or all of the processing of the data collected using an OCT probe, an FFR probe, an angiography system, and other imaging and subject monitoring devices and the processor-based system is implemented as a set of computer program instructions that is converted into a computer executable form, stored as such in a computer readable medium, and executed by a microprocessor under the control of an operating system. Thus, user interface instructions and triggers based upon the completion of a pullback or a co-registration request, for example, are transformed into processor understandable instructions suitable for generating OCT data, performing image processing using various and other features and embodiments described above.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies (e.g., Bluetooth), networking technologies, and internetworking technologies. The computer program may be distributed in any form as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink-wrapped software), preloaded with a computer system (e.g., on system ROM or fixed disk), or distributed from a server or electronic bulletin board over the communication system (e.g., the internet or World Wide Web).

Various examples of suitable processing modules are discussed below in more detail. As used herein a module refers to software, hardware, or firmware suitable for performing a specific data processing or data transmission task. In one embodiment, a module refers to a software routine, program, or other memory resident application suitable for receiving, transforming, routing performing feature extraction and processing instructions, or various types of data such as angiography data, OCT data, IVUS data, cross frame data, pixel coordinates, clusters, clouds, opaque regions, centerlines, shadows, pixels, clusters, distance metrics, intensity patterns, anatomic features, anatomic landmarks, bifurcations, bends, and other information of interest as described herein.

Computers and computer systems described herein may include operatively associated computer-readable media such as memory for storing software applications used in obtaining, processing, storing and/or communicating data. It can be appreciated that such memory can be internal, external, remote or local with respect to its operatively associated computer or computer system.

Memory may also include any means for storing software or other instructions including, for example and without limitation, a hard disk, an optical disk, floppy disk, DVD (digital versatile disc), CD (compact disc), memory stick, flash memory, ROM (read only memory), RAM (random access memory), DRAM (dynamic random access memory), PROM (programmable ROM), EEPROM (extended erasable PROM), and/or other like computer-readable media.

In general, computer-readable memory media applied in association with embodiments of the disclosure described herein may include any memory medium capable of storing instructions executed by a programmable apparatus. Where applicable, method steps described herein may be embodied or executed as instructions stored on a computer-readable memory medium or memory media. These instructions may be software embodied in various programming languages such as C++, C, Java, and/or a variety of other kinds of software programming languages that may be applied to create instructions in accordance with embodiments of the disclosure.

The aspects, embodiments, features, and examples of the disclosure are to be considered illustrative in all respects and are not intended to limit the disclosure, the scope of which is defined only by the claims. Other embodiments, modifications, and usages will be apparent to those skilled in the art without departing from the spirit and scope of the claimed disclosure.

The use of headings and sections in the application is not meant to limit the disclosure; each section can apply to any aspect, embodiment, or feature of the disclosure.

Throughout the application, where compositions are described as having, including, or comprising specific components, or where processes are described as having, including or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components and can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise. As used herein, the term "about" refers to a ±10% variation from the nominal value.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

It should be appreciated that various aspects of the claimed disclosure are directed to subsets and substeps of the techniques disclosed herein. Further, the terms and expressions employed herein are used as terms of description and not of limitation, and there is no intention, in the use of such terms and expressions, of excluding any equivalents of the features shown and described or portions thereof, but it is recognized that various modifications are possible within the scope of the disclosure claimed. Accordingly, what is desired to be secured by Letters Patent is the disclosure as defined and differentiated in the following claims, including all equivalents.

What is claimed is:

1. A processor-based method of detecting one or more regions of interest in one or more x-ray images, the method comprising:
    storing a set of angiography image frames obtained during a first time period in an electronic memory device;
    detecting a guidewire in one or more frames of the set;
    generating vessel centerlines in one or more frames of the set;
    detecting arterial segments comprising anchor points, bifurcation or bends in one or more frames of the set;
    generating a plurality of cross-frame positions by performing arc length interpolation with regard to a group of frames, the group of frames comprising:
    one or more frames comprising a detected guidewire and
    one or more frames comprising one or more of the detected arterial segments; and
    performing cross-frame registration of the set of angiography image frames using the plurality of cross-frame positions.

2. The method of claim 1 further comprising
    detecting a plurality of candidate contrast cloud regions in one or more angiography frames.

3. The method of claim 2 further comprising excluding regions of one or more of the angiography frames identified as comprising a contrast cloud region from a centerline generation process.

4. The method of claim 2 further comprising defining a proximal endpoint of one or more vessel centerlines using an endpoint selected from one or more of the candidate contrast cloud regions.

5. The method of claim 4 further comprising defining a distal endpoint of one or more vessel centerlines using an endpoint of a detected guidewire.

6. The method of claim 1, wherein detecting the guidewire in one or more frames of the set comprises detecting guidewire fragments and joining them based on a take off angle and a separation distance and further comprising defining a distal endpoint of one or more vessel centerlines using an endpoint of a detected guidewire.

7. The method of claim 1 further comprising identifying a plurality of anatomic features in one or more of the frames.

8. The method of claim 7 wherein identifying an anatomic feature comprises generating a cluster comprising a set of detected anatomic features across a plurality of frames, wherein the cluster is indicative of the detected anatomic feature being the same anatomic feature imaged at different times on different frames.

9. The method of claim 1 further comprising performing an intravascular data collection probe pullback during the first time period.

10. The method of claim 1 wherein detecting a guidewire in one or more frames of the set comprises
    applying a ridge enhancing filter to the one or more frames of the set,
    adaptively thresholding the filtered angiography frame one or more frames of the set, wherein the adaptive thresholding rejects image areas based on intensity;
    operating on the adaptively thresholded angiography frame using an intensity filter to generate an intensity filtered frame; and
    detecting a guidewire portion in the intensity filtered frame.

11. The method of claim 10 further comprising applying a morphological filter.

12. A system for detecting one or more features in an angiographic image, the system comprising:
    one or more memory devices; and
    a computing device in communication with the memory device, wherein the memory device comprises instructions executable by the computing device to cause the computing device to:
    store a set of angiography image frames obtained during a first time period in an electronic memory device;
    detect a guidewire in one or more frames of the set;
    generate vessel centerlines in one or more frames of the set;
    detect arterial segments comprising anchor points, bifurcation or bends in one or more frames of the set;
    generate a plurality of cross-frame positions by performing arc length interpolation with regard to a group of frames, the group of frames comprising:
    one or more frames comprising a detected guidewire and
    one or more frames comprising one or more of the detected arterial segments; and
    perform cross-frame registration of the set of angiography image frames using the plurality of cross-frame positions.

13. The system of claim 12 wherein the computing device comprises further instructions to detect a plurality of candidate contrast cloud regions in one or more angiography frames.

14. The system of claim 13 wherein the computing device comprises further instructions to define a proximal endpoint of one or more vessel centerlines using an endpoint selected from one or more of the candidate contrast cloud regions.

15. The system of claim 14 wherein the computing device comprises further instructions to define a distal endpoint of one or more vessel centerlines using an endpoint of a detected guidewire.

16. The system of claim 12 wherein the computing device comprises further instructions to define a distal endpoint of one or more vessel centerlines using an endpoint of a detected guidewire.

17. The system of claim 12 wherein the computing device comprises further instructions such that detecting a guidewire in one or more frames of the set comprises
- applying a plurality of filters to an angiography image frame;
- adaptively thresholding the filtered angiography frame;
- operating on the adaptively thresholded angiography frame using an intensity filter to generate an intensity filtered frame; and
- detecting a guidewire portion in the intensity filtered frame.

18. The system of claim 17 wherein the plurality of filters comprises a morphological filter and a ridge enhancing filter.

* * * * *